(12) United States Patent
Kim et al.

(10) Patent No.: US 11,319,386 B2
(45) Date of Patent: May 3, 2022

(54) MODIFIED CONJUGATED DIENE-BASED POLYMER AND METHOD FOR PREPARING THE SAME

(71) Applicant: LG Chem, Ltd., Seoul (KR)

(72) Inventors: Ji Eun Kim, Daejeon (KR); Eun Gyeong Lee, Daejeon (KR); Dae June Joe, Daejeon (KR); Won Mun Choi, Daejeon (KR)

(73) Assignee: LG Chem, Ltd.

( * ) Notice: Subject to any disclaimer, the term of this patent is extended or adjusted under 35 U.S.C. 154(b) by 293 days.

(21) Appl. No.: 16/651,653

(22) PCT Filed: Oct. 18, 2018

(86) PCT No.: PCT/KR2018/012367
§ 371 (c)(1),
(2) Date: Mar. 27, 2020

(87) PCT Pub. No.: WO2019/078653
PCT Pub. Date: Apr. 25, 2019

(65) Prior Publication Data
US 2020/0308368 A1    Oct. 1, 2020

(30) Foreign Application Priority Data

Oct. 20, 2017 (KR) .................. 10-2017-0136711

(51) Int. Cl.
*C08C 19/22*     (2006.01)
*C08F 8/30*      (2006.01)
*C08F 36/04*     (2006.01)
*C07F 7/10*      (2006.01)
*C07C 229/16*    (2006.01)

(52) U.S. Cl.
CPC ............ *C08C 19/22* (2013.01); *C08F 8/30* (2013.01); *C08F 36/04* (2013.01)

(58) Field of Classification Search
USPC .............................. 556/412; 525/342; 528/33
See application file for complete search history.

(56) References Cited

U.S. PATENT DOCUMENTS

| 7,767,774 | B2 | 8/2010 | Suzuki et al. |
| 10,174,133 | B2 | 1/2019 | Choi et al. |
| 2008/0033110 | A1 | 2/2008 | Suzuki et al. |
| 2011/0077325 | A1 | 3/2011 | Luo |
| 2014/0213721 | A1 | 7/2014 | Yamada et al. |
| 2017/0204205 | A1 | 7/2017 | Choi et al. |

FOREIGN PATENT DOCUMENTS

| CN | 1961011 A | 5/2007 | |
| CN | 107074987 A | 8/2017 | |
| EP | 3312203 A1 * | 4/2018 | ............... C08F 8/30 |
| JP | H0657767 B2 | 8/1994 | |
| JP | 2011079882 A | 4/2011 | |
| JP | 2012087200 A | 5/2012 | |
| JP | 2013506740 A | 2/2013 | |
| JP | 2013060525 A | 4/2013 | |
| JP | 2017538790 A | 12/2017 | |
| KR | 20140098716 A | 8/2014 | |
| KR | 20160065016 A | 6/2016 | |
| KR | 20160076161 A | 6/2016 | |
| WO | 2011041534 A1 | 4/2011 | |
| WO | 2013035589 A1 | 3/2013 | |

OTHER PUBLICATIONS

International Search Report for Application No. PCT/KR2018/012367, dated Apr. 12, 2019, pp. 1-2.
Chinese Search Report for Application No. 201880060832.9, dated May 6, 2021, 3 pages.

* cited by examiner

*Primary Examiner* — Fred M Teskin
(74) *Attorney, Agent, or Firm* — Lerner, David, Littenberg, Krumholz & Mentlik, LLP

(57) ABSTRACT

The present invention relates to a modifier represented by Formula 1, a method for preparing the same, a modified conjugated diene-based polymer including a functional group derived from the modifier and having a high modification ratio, and a method for preparing the polymer.

16 Claims, No Drawings

MODIFIED CONJUGATED DIENE-BASED POLYMER AND METHOD FOR PREPARING THE SAME

CROSS-REFERENCE TO RELATED APPLICATIONS

The present application is a national phase entry under 35 U.S.C. § 371 of International Application No. PCT/KR2018/012367 filed Oct. 18, 2018, which claims priority from Korean Patent Application No. 10-2017-0136711 filed Oct. 20, 2017, all of which are incorporated herein by reference.

TECHNICAL FIELD

The present invention relates to a modifier having a specific structure, a method for preparing the same, a modified conjugated diene-based polymer including a functional group derived from the modifier and having a high modification ratio, and a method for preparing the polymer.

BACKGROUND ART

According to the recent demand for cars having a low fuel consumption ratio, a conjugated diene-based polymer having modulational stability represented by wet skid resistance as well as low rolling resistance, and excellent abrasion resistance and tensile properties is required as a rubber material for tires.

In order to reduce the rolling resistance of tires, there is a method of reducing hysteresis loss of vulcanized rubber, and rebound resilience at 50° C. to 80° C., tan δ, Goodrich heating, or the like is used as an evaluation index of the vulcanized rubber. That is, it is desirable to use a rubber material having high rebound resilience at the above temperature or a low tan δ value or Goodrich heating.

Natural rubbers, polyisoprene rubbers, or polybutadiene rubbers are known as rubber materials having low hysteresis loss, but these rubbers have a limitation of low wet skid resistance. Thus, recently, conjugated diene-based (co)polymers such as styrene-butadiene rubbers (hereinafter, referred to as "SBR") and butadiene rubbers (hereinafter, referred to as "BR"), are prepared by emulsion polymerization or solution polymerization to be used as rubbers for tires.

In case where the BR or SBR is used as a rubber material for tires, generally, a filler such as silica and carbon black is blended and used to attain the physical properties required for tires. However, since the affinity of the BR or SBR with a filler is not good, physical properties such as abrasion resistance, crack resistance and processability are rather degraded.

Accordingly, as a method for improving the dispersibility of SBR with a filler such as silica and carbon black, a method of modifying the polymerization active part of a conjugated diene-based polymer obtained by anionic polymerization using an organolithium with a functional group that may interact with the filler, has been suggested. For example, a method of modifying the polymerization active terminal of a conjugated diene-based polymer with a tin-based compound, a method of introducing an amino group, or a method of modifying with an alkoxysilane derivative has been suggested.

In addition, as a method for improving the dispersibility of BR with a filler such as silica and carbon black, a method of modifying a living active terminal with a specific coupling agent or a modifier in a living polymer obtained by coordination polymerization using a catalyst composition including a lanthanide rare earth element compound, has been developed.

However, the BR or SBR modified by the above-mentioned method has a low terminal modification ratio, and the improving effect of physical properties in a tire manufactured using the same is insignificant.

DISCLOSURE OF THE INVENTION

Technical Problem

The present invention has been devised to solve the above-mentioned problems of the conventional technique, and an object of the present invention is to provide a modifier useful for modifying a polymer.

Another object of the present invention is to provide a method for preparing the modifier.

Another object of the present invention is to provide a modified conjugated diene-based polymer including a functional group derived from the modifier and having a high modification ratio.

Further, another object of the present invention is to provide a method for preparing the modified conjugated diene-based polymer.

Technical Solution

To solve the above-described tasks, there is provided in the present invention a modifier represented by the following Formula 1:

[Formula 1]

$$R^1-R^2 \diagdown N-R^4-N \diagup R^5 \diagup R^3 \diagdown R^6-R^7$$

in Formula 1,
$R^1$— is —COOR$^8$,
$R^2$ and $R^6$ are each independently a divalent hydrocarbon group of 2 to 20 carbon atoms,
$R^3$ and $R^5$ are each independently —SiR$^9$R$^{10}$R$^{11}$,
$R^4$ is a divalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms,
$R^7$ is —COOR$^{12}$,
where $R^8$ and $R^{12}$ are each independently a monovalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms, and
$R^9$ to $R^{11}$ are each independently a monovalent hydrocarbon group of 1 to 20 carbon atoms, or a monovalent hydrocarbon group of 1 to 20 carbon atoms including one or more heteroatoms selected from the group consisting of N, S and O.

In addition, there is provided in the present invention, a method for preparing a modifier represented by Formula 1, including performing first reaction between a compound represented by Formula 4 below and a compound represented by Formula 5 below to prepare a compound represented by Formula 6 below (step a); and performing second reaction between the compound represented by Formula 6 below and a compound represented by Formula 7 below (step b):

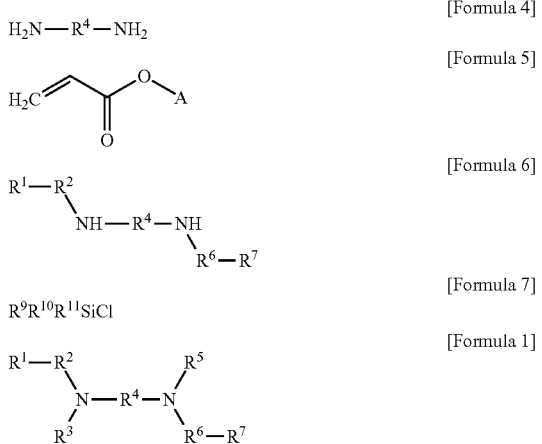

[Formula 4]
[Formula 5]
[Formula 6]
[Formula 7]
[Formula 1]

in Formula 1, and Formula 4 to Formula 7, $R^1$— is —$COOR^8$, $R^2$ and $R^6$ are each independently a divalent hydrocarbon group of 2 to 20 carbon atoms, $R^3$ and $R^5$ are each independently —$SiR^9R^{10}R^{11}$, $R^4$ is a divalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms, and an aryl group of 6 to 30 carbon atoms, $R^7$ is —$COOR^{12}$, A is $R^8$ or $R^{12}$, where $R^8$ and $R^{12}$ are each independently a monovalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms, and an aryl group of 6 to 30 carbon atoms, and $R^9$ to $R^{11}$ are each independently a monovalent hydrocarbon group of 1 to 20 carbon atoms, or a monovalent hydrocarbon group of 1 to 20 carbon atoms including one or more heteroatoms selected from the group consisting of N, S and O.

Also, there is provided in the present invention a modified conjugated diene-based polymer including a functional group derived from the modifier represented by Formula 1.

Further, there is provided in the present invention a method for preparing a modified conjugated diene-based polymer, including polymerizing a conjugated diene-based monomer in the presence of a catalyst composition including a lanthanide rare earth element-containing compound in a hydrocarbon solvent to prepare an active polymer which is combined with an organometal (step 1); and reacting the active polymer with the modifier represented by Formula 1 (step 2).

Advantageous Effects

The modifier represented by Formula 1 according to the present invention includes a polymer reactive functional group, for example, two ester groups, and has high anion reactivity and may easily act with the active part of a polymer, thereby easily performing modification.

Also, during modifying the modified conjugated diene-based polymer according to the present invention, since an amine group protected by a trialkylsilyl group, etc. may be hydrolyzed in a subsequent treatment process to produce two secondary amine groups, the affinity with a filler such as carbon black may be improved to an excellent degree, and a fuel consumption ratio may be improved.

Also, since the method for preparing a modified conjugated diene-based polymer according to the present invention uses the modifier represented by Formula 1, a modified conjugated diene-based polymer having a high modification ratio may be easily prepared.

BEST MODE FOR CARRYING OUT THE INVENTION

Hereinafter, the present invention will be described in more detail in order to assist the understanding of the present invention.

It will be understood that words or terms used in the description and claims of the present invention shall not be interpreted as the meaning defined in commonly used dictionaries. It will be further understood that the words or terms should be interpreted as having a meaning that is consistent with their meaning of the technical idea of the invention, based on the principle that an inventor may properly define the concept of the words to best explain the invention.

The present invention provides a modifier useful for the modification of a modified conjugated diene-based polymer.

The modifier according to an embodiment of the present invention is characterized in being represented by the following Formula 1:

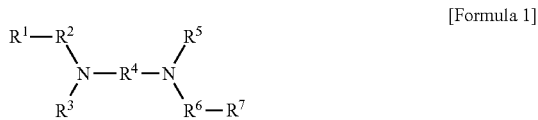

[Formula 1]

in Formula 1, $R^1$— is —$COOR^8$, $R^2$ and $R^6$ are each independently a divalent hydrocarbon group of 2 to 20 carbon atoms, $R^3$ and $R^5$ are each independently —$SiR^9R^{10}R^{11}$, $R^4$ is a divalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms, $R^7$ is —$COOR^{12}$, where $R^8$ and $R^{12}$ are each independently a monovalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms, and $R^9$ to $R^{11}$ are each independently a monovalent hydrocarbon group of 1 to 20 carbon atoms, or a monovalent hydrocarbon group of 1 to 20 carbon atoms including one or more heteroatoms selected from the group consisting of N, S and O.

Particularly, in Formula 1, $R^1$— may be —$COOR^8$, $R^7$ may be —$COOR^{12}$, and $R^8$ and $R^{12}$ may be each independently a monovalent hydrocarbon group of 1 to 20 carbon atoms, which is unsubstituted or substituted with a substituent.

If $R^8$ and $R^{12}$ are each independently an unsubstituted monovalent hydrocarbon group of 1 to 20 carbon atoms, $R^8$ and $R^{12}$ may be each independently selected from the group consisting of an alkyl group of 1 to 20 carbon atoms, a cycloalkyl group of 3 to 20 carbon atoms, an aryl group of 6 to 20 carbon atoms and an arylalkyl group of 7 to 20 carbon atoms, and particularly, $R^8$ and $R^{12}$ may be each independently selected from the group consisting of an alkyl group of 1 to 10 carbon atoms, a cycloalkyl group of 3 to 12 carbon atoms, an aryl group of 6 to 12 carbon atoms and an arylalkyl group of 7 to 12 carbon atoms.

In addition, if $R^8$ and $R^{12}$ are each independently a substituted monovalent hydrocarbon group of 1 to 20 carbon atoms with a substituent, $R^8$ and $R^{12}$ may be each independently an alkyl group of 1 to 10 carbon atoms, which is substituted with one or more substituents selected from the group consisting of a linear or branched alkyl group of 1 to 20 carbon atoms, a cycloalkyl group of 3 to 20 carbon atoms and an aryl group of 6 to 30 carbon atoms.

In addition, in Formula 1, $R^2$ and $R^6$ may be each independently a divalent hydrocarbon group of 2 to 20 carbon atoms, particularly, an alkylene group of 2 to 10 carbon atoms. More particularly, $R^2$ and $R^6$ may be each independently an alkylene group of 2 to 7 carbon atoms.

In addition, in Formula 1, $R^3$ and $R^5$ are each independently —$SiR^9R^{10}R^{11}$, where $R^9$, $R^{10}$ and $R^{11}$ may be each independently a monovalent hydrocarbon group of 1 to 20 carbon atoms, or a monovalent hydrocarbon group of 1 to 20 carbon atoms including one or more heteroatoms selected from the group consisting of N, S and O.

If $R^9$, $R^{10}$ and $R^{11}$ are each independently a monovalent hydrocarbon group of 1 to 20 carbon atoms, $R^9$, $R^{10}$ and $R^{11}$ may be each independently selected from the group consisting of an alkyl group of 1 to 20 carbon atoms, a cycloalkyl of 3 to 20 carbon atoms, an aryl group of 6 to 20 carbon atoms, and an arylalkyl group of 7 to 20 carbon atoms, and particularly, $R^9$, $R^{10}$ and $R^{11}$ may be each independently selected from the group consisting of an alkyl group of 1 to 10 carbon atoms, a cycloalkyl of 3 to 12 carbon atoms, an aryl group of 6 to 12 carbon atoms and an arylalkyl group of 7 to 12 carbon atoms.

In addition, if $R^9$, $R^{10}$ and $R^{11}$ are each independently a monovalent hydrocarbon group of 1 to 20 carbon atoms, including a heteroatom, $R^9$, $R^{10}$ and $R^{11}$ may each independently include one or more heteroatoms instead of carbon atoms in the hydrocarbon group; or may be a hydrocarbon group in which one or more hydrogen atoms bonded to carbon atoms in the hydrocarbon group are substituted with heteroatoms or functional groups including a heteroatom. Particularly, if $R^9$, $R^{10}$ and $R^{11}$ are each independently a monovalent hydrocarbon group of 1 to 20 carbon atoms, including a heteroatom, $R^9$, $R^{10}$ and $R^{11}$ may be each independently an alkoxy group; a phenoxy group; a carboxyl group; an acid anhydride group; an amino group; an amide group; an epoxy group; a mercapto group; —$[R^{13}O]xR^{14}$ (where $R^{13}$ is an alkylene group of 2 to 20 carbon atoms, $R^{14}$ is selected from the group consisting of a hydrogen atom, an alkyl group of 1 to 20 carbon atoms, a cycloalkyl group of 3 to 20 carbon atoms, an aryl group of 6 to 20 carbon atoms and an arylalkyl group of 7 to 20 carbon atoms, and x is an integer of 2 to 10); or a monovalent hydrocarbon group of 1 to 20 carbon atoms including one or more functional groups selected from the group consisting of a hydroxyl group, an alkoxy group, a phenoxy group, a carboxyl group, an ester group, an acid anhydride group, an amino group, an amide group, an epoxy group and a mercapto group (for example, a hydroxyalkyl group, an alkoxyalkyl group, a phenoxyalkyl group, an aminoalkyl group or a thioalkyl group). More particularly, if $R^9$, $R^{10}$ and $R^{11}$ are each independently an alkyl group of 1 to 20 carbon atoms, including a heteroatom, $R^9$, $R^{10}$ and $R^{11}$ may be each independently selected from the group consisting of an alkoxy group of 1 to 20 carbon atoms, an alkoxyalkyl group of 2 to 20 carbon atoms, a phenoxyalkyl group of 7 to 20 carbon atoms, an aminoalkyl group of 1 to 20 carbon atoms and —$[R^{13}O]xR^{14}$ (where $R^{13}$ is an alkylene group of 2 to 20 carbon atoms, $R^{14}$ is selected from the group consisting of a hydrogen atom, an alkyl group of 1 to 10 carbon atoms, a cycloalkyl group of 3 to 12 carbon atoms, an aryl group of 6 to 18 carbon atoms and an arylalkyl group of 7 to 18 carbon atoms, and x is an integer of 2 to 10).

In addition, in Formula 1, $R^4$ may be a divalent hydrocarbon group of 1 to 20 carbon atoms or a divalent hydrocarbon group of 1 to 20 carbon atoms, which is substituted with a substituent.

If $R^4$ is the divalent hydrocarbon group of 1 to 20 carbon atoms, $R^4$ may be an alkylene group of 1 to 10 carbon atoms such as a methylene group, an ethylene group and a propylene group; an arylene group of 6 to 20 carbon atoms such as a phenylene group; or an arylalkylene group of 7 to carbon atoms as the combination thereof. More particularly, $R^4$ may be an alkylene group of 1 to 10 carbon atoms. In addition, if $R^4$ is the divalent hydrocarbon group of 1 to 20 carbon atoms, which is substituted with a substituent, $R^4$ may be an alkylene group of 1 to 10 carbon atoms, which is substituted with one or more substituents selected from the group consisting of a linear or branched alkyl group of 1 to 20 carbon atoms, a cycloalkyl group of 3 to 20 carbon atoms and an aryl group of 6 to 30 carbon atoms.

Particularly, the modifier may be Formula 1, in which $R^1$— is —$COOR^8$, $R^7$ is —$COOR^{12}$, where $R^8$ and $R^{12}$ are each independently an alkyl group of 1 to 10 carbon atoms, which is unsubstituted or substituted with a linear or branched alkyl group of 1 to 10 carbon atoms, $R^2$, $R^4$ and $R^6$ are each independently an alkylene group of 2 to 10 carbon atoms, $R^3$ and $R^5$ are each independently —$SiR^9R^{10}R^{11}$, where $R^9$ to $R^{10}$ are each independently any one selected from the group consisting of an alkyl group of 1 to 10 carbon atoms, a cycloalkyl group of 3 to 12 carbon atoms, an aryl group of 6 to 12 carbon atoms, an arylalkyl group of 7 to 12 carbon atoms, an alkoxyalkyl group of 2 to 10 carbon atoms, a phenoxyalkyl group of 7 to 12 carbon atoms and an aminoalkyl group of 1 to 10 carbon atoms.

More particularly, the modifier represented by Formula 1 may be a compound represented by the following Formula 2 or Formula 3:

[Formula 2]

-continued

[Formula 3]

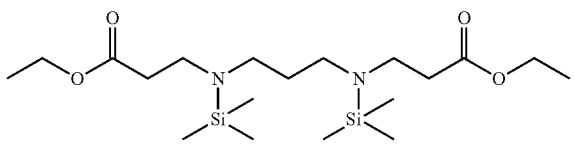

The solubility of the modifier with respect to 100 g of a nonpolar solvent, for example, n-hexane, at 25° C. under 1 atm, may be 10 g or more. Here, the solubility of the modifier means the degree of clear dissolution without turbidity if observed with the naked eye. Accordingly, the modifier according to an embodiment of the present invention may be used as a modifier for a polymer and may improve the modification ratio of the polymer.

In addition, the modifier represented by Formula 1 according to the present invention includes a reactive functional group with respect to a conjugated diene-based polymer, a functional group having affinity with a filler and a functional group having affinity with a solvent, and may easily modify a conjugated diene-based polymer with a high modification ratio, and thus, the abrasion resistance, low fuel consumption properties and processability of a rubber composition including the same, and a molded article manufactured therefrom such as a tire, may be improved. Particularly, the modifier of Formula 1 may include a reactive functional group with respect to a polymer in a molecule (in Formula 1, substituents corresponding to $R^1$ and $R^7$), an amine group and an alkyl chain, and the reactive functional group shows high reactivity with respect to the active part of the conjugated diene-based polymer to modify the conjugated diene-based polymer with a high modification ratio, and as a result, a functional group which is substituted in the modifier may be introduced into the conjugated diene-based polymer in a high yield.

In addition, the amine group may be present in a protected state by the substituents corresponding to $R^3$ and $R^5$ in Formula 1, and then, after finishing the modification of a polymer, may be hydrolyzed in a subsequent process into two secondary amine groups. In this case, due to the interaction between the secondary amine group and the functional group having affinity with a filler, the affinity with a filler, particularly, silica or carbon black, may be further improved when compared with a modified conjugated diene-based polymer in which a secondary amine group is not present or a modified conjugated diene-based polymer in which less than two secondary amine groups are present. The improved interaction with the filler may server fuel consumption ratio improving effect of a rubber composition.

Here, amine means a nitrogen compound obtained by substituting a hydrogen atom in ammonia with a substituent such as an alkyl group and an aryl group. The amine group means a functional group including the nitrogen compound. In addition, a secondary amine group means a functional group including a nitrogen compound obtained by substituting two hydrogen atoms in ammonia with substituents.

In addition, the alkyl chain may increase the affinity with a polymerization solvent and increase the solubility of the modifier, and thus, a modification ratio with respect to a conjugated diene polymer may be increased.

In addition, there is provided in the present invention a method for preparing a modifier represented by Formula 1.

The preparation method according to an embodiment of the present invention is characterized in including performing first reaction between a compound represented by Formula 4 below and a compound represented by Formula 5 below to prepare a compound represented by Formula 6 below (step a); and performing second reaction between the compound represented by Formula 6 below and a compound represented by Formula 7 below (step b):

[Formula 4]

[Formula 5]

[Formula 6]

[Formula 7]

$R^9R^{10}R^{11}SiCl$

[Formula 1]

in Formula 1, $R^1$ is —COOR$^8$, $R^2$ and $R^6$ are each independently a divalent hydrocarbon group of 2 to 20 carbon atoms, $R^3$ and $R^5$ are each independently —SiR$^9$R$^{10}$R$^{11}$, $R^4$ is a divalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms, $R^7$ is —COOR$^{12}$, A is $R^8$ or $R^{12}$, where $R^8$ and $R^{12}$ are each independently a monovalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms, and $R^9$ to $R^{11}$ are each independently a monovalent hydrocarbon group of 1 to 20 carbon atoms, or a monovalent hydrocarbon group of 1 to 20 carbon atoms including one or more heteroatoms selected from the group consisting of N, S and O.

A particular modifier represented by Formula 1 may be the same as described above.

In addition, the compound represented by Formula 5 may include a compound where A is $R^8$, or a compound where A is $R^{12}$, or may include both the two kinds of the compounds.

The first reaction of step a is a step for preparing the compound represented by Formula 6, and may be performed by performing first reaction between the compound represented by Formula 4 and the compound represented by Formula 5. In this case, the compound represented by Formula 4 and the compound represented by Formula 5 may be used in a stoichiometric ratio, and particularly, the compound represented by Formula 4 and the compound represented by Formula 5 may be used in a molar ratio of 1:1 to 1:3 (compound represented by Formula 4: compound represented by Formula 5). More particularly, the compound represented by Formula 4 and the compound represented by Formula 5 may be used in a molar ratio of 1:1.8 to 1:2.5, more particularly, 1:2.

Here, the first reaction may be performed in a temperature range of 5° C. to 60° C., particularly, 10° C. to 35° C.

The second reaction of step b is a step for preparing the modifier represented by Formula 1, and may be performed by reacting the compound represented by Formula 6 and the compound represented by Formula 7. In this case, the compound represented by Formula 6 and the compound represented by Formula 7 may be used in a stoichiometric ratio, for example, the compound represented by Formula 6 and the compound represented by Formula 7 may be used in a molar ratio of 1:2 to 1:4 (compound represented by Formula 6: compound represented by Formula 7), particularly, in a molar ratio of 1:2 to 1:3, more particularly, 1:2.4. Meanwhile, the second reaction may be performed by adding the compound represented by Formula 7 to the compound represented by Formula 6 in temperature range conditions of −10° C. to 20° C., particularly, −10° C. to 10° C., and then continuously reacting while increasing the temperature to a temperature range of 0° C. to 35° C.

In addition, before or after adding the compound represented by Formula 7 to the compound represented by Formula 6, a base may be further included, and preferably, before adding the compound represented by Formula 7, a base may be further added. Here, the equivalent ratio of the compound represented by Formula 6 and the base (compound of Formula 6: base) may be 1:2 to 1:5, particularly, 1:2 to 1:4, more particularly, 1:3. In addition, the base may particularly be a compound represented by the following Formula 8:

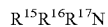   [Formula 8]

where $R^{15}$ to $R^{17}$ are each independently a monovalent hydrocarbon group of 1 to 20 carbon atoms.

Particularly, $R^{15}$, $R^{16}$ and $R^{17}$ may be each independently selected from the group consisting of an alkyl group of 1 to 20 carbon atoms, a cycloalkyl group of 3 to 20 carbon atoms, an aryl group of 6 to 20 carbon atoms and an arylalkyl group of 7 to 20 carbon atoms, and particularly, $R^{15}$, $R^{16}$ and $R^{17}$ may be each independently selected from the group consisting of an alkyl group of 1 to 10 carbon atoms, a cycloalkyl group of 3 to 12 carbon atoms, an aryl group of 6 to 12 carbon atoms and an arylalkyl group of 7 to 12 carbon atoms.

The base is not specifically limited, and may preferably be selected from triethylamine (TEA) or diisopropylethylamine (DIPEA, Hunig's base).

Also, there is provided in the present invention a modified conjugated diene-based polymer including a functional group derived from a modifier represented by the following Formula 1:

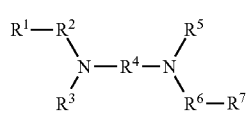   [Formula 1]

in Formula 1,
$R^1$— is —COOR$^8$,
$R^2$ and $R^6$ are each independently a divalent hydrocarbon group of 2 to 20 carbon atoms,
$R^3$ and $R^5$ are each independently —SiR$^9$R$^{10}$R$^{11}$, $R^4$ is a divalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms, $R^7$ is —COOR$^{12}$, where $R^8$ and $R^{12}$ are each independently a monovalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms, and $R^9$ to $R^{11}$ are each independently a monovalent hydrocarbon group of 1 to 20 carbon atoms, or a monovalent hydrocarbon group of 1 to 20 carbon atoms including one or more heteroatoms selected from the group consisting of N, S and O.

A particular modifier represented by Formula 1 may be the same as described above.

The modified conjugated diene-based polymer according to an embodiment of the present invention may be prepared by reacting an active polymer combined with an organometal with the modifier represented by Formula 1 by a preparation method which will be explained layer, and the modified conjugated diene-based polymer may show improved physical properties by including a functional group derived from the modifier represented by Formula 1.

Particularly, the modified conjugated diene-based polymer may include a functional group having affinity with a filler and a functional group having affinity with a solvent by including the functional group derived from the modifier represented by Formula 1, and the abrasion resistance, low fuel consumption properties and processability of a rubber composition including the same and a molded article manufactured therefrom such as a tire, may be improved.

The modified conjugated diene-based polymer may have a number average molecular weight (Mn) of 100,000 g/mol to 700,000 g/mol, particularly, 120,000 g/mol to 500,000 g/mol.

In addition, the modified conjugated diene-based polymer may have a weight average molecular weight (Mw) of 300,000 g/mol to 1,200,000 g/mol, particularly, 400,000 g/mol to 1,000,000 g/mol.

In addition, the modified conjugated diene-based polymer may have molecular weight distribution (Mw/Mn) of 1.05 to 5, particularly, 1.05 to 3.4.

Also, if applied to a rubber composition, considering the improving effects of the mechanical properties, elasticity and processability of the rubber composition with good balance, the modified conjugated diene-based polymer according to an embodiment of the present invention may have the above-mentioned molecular weight distribution range and at the same time, may satisfy the range conditions of the weight average molecular weight and the number average molecular weight.

Particularly, the modified conjugated diene-based polymer may have molecular weight distribution of 1.05 to 5, a weight average molecular weight of 300,000 g/mol to 1,200,000 g/mol, and a number average molecular weight of 100,000 g/mol to 700,000 g/mol, more particularly, molecular weight distribution of 1.05 or 3.4, a weight average molecular weight of 400,000 g/mol to 1,000,000 g/mol, and a number average molecular weight of 120,000 g/mol to 500,000 g/mol.

Here, each of the weight average molecular weight and the number average molecular weight is a conversion molecular weight with polystyrene standard, analyzed by gel permeation chromatography (GPC), and the molecular weight distribution (Mw/Mn) is also called as poly dispersibility or polydispersity and is calculated as the ratio (Mw/Mn) of the weight average molecular weight (Mw) and the number average molecular weight (Mn).

In addition, the modified conjugated diene-based polymer according to an embodiment of the present invention may be a polymer having high linearity of which —stress/relaxation (—S/R) value at 100° C. is 0.7 or more. In this case, the —S/R represents stress change shown as the response with respect to the same amount of strain generated in a material, and is an index representing the linearity of a polymer. Generally, it means that if the —S/R value decreases, the degree of linearity of the polymer decreases, and if the linearity decreases, if applied to a rubber composition, rolling resistance or rotation resistance may increase. In addition, the degree of branching and molecular weight distribution of a polymer may be expected from the —S/R value, and if the —S/R value decreases, the degree of branching increases and molecular weight distribution increases, and as a result, the processability of the polymer becomes good but the mechanical properties are degraded.

The modified conjugated diene-based polymer according to an embodiment of the present invention has a high —S/R value of 0.7 or more at 100° C. as described above, and if applied to a rubber composition, resistance properties and fuel consumption properties may become excellent. Particularly, the —S/R value of the modified conjugated diene-based polymer may be 0.7 to 1.0.

Here, the —S/R value was measured using a mooney viscosity system, for example, a Large Rotor of MV2000E of Monsanto Co., Ltd. in the conditions of 100° C. and a rotor speed of 2±0.02 rpm. Particularly, a polymer was stood at room temperature (23±5° C.) for 30 minutes or more, and 27±3 g of the specimen was collected and put in a die cavity, and then, Platen was operated to measure the mooney viscosity while applying torque. In addition, the —S/R value was obtained by measuring the gradient value of the mooney viscosity change appearing during releasing the torque.

In addition, particularly, the modified conjugated diene-based polymer may have the cis-1,4 bond content of a conjugated diene of 95% or more, more particularly, 98% or more, if measured by Fourier transform infrared spectrometry (FT-IR). Accordingly, if applied to a rubber composition, the abrasion resistance, crack resistance and ozone resistance of the rubber composition may be improved.

In addition, the modified conjugated diene-based polymer may have the vinyl content of a conjugated diene part of 5% or less, more particularly, 3% or less, if measured by Fourier transform infrared spectrometry. If the vinyl content in the polymer is greater than 5%, the abrasion resistance, crack resistance and ozone resistance of a rubber composition including the same may be degraded.

Here, each of the cis-1,4 bond content and the vinyl content in the polymer by the Fourier transform infrared spectroscopy (FT-IR) is obtained by measuring FT-IR transmittance spectrum of the carbon disulfide solution of a conjugated diene-based polymer that is prepared at a concentration of 5 mg/ml with carbon disulfide of the same cell as a blank, and using the maximum peak value around 1130 cm$^{-1}$ (a, base line) of the measured spectrum, the minimum peak value around 967 cm$^{-1}$ (b) showing a trans-1,4 bond, the minimum peak value around 911 cm$^{-1}$ (c) showing a vinyl bond, and the minimum peak value around 736 cm$^{-1}$ (d) showing a cis-1,4 bond.

Also, there is provided in the present invention a method for preparing a modified conjugated diene-based polymer including a functional group derived from the modifier represented by Formula 1.

The preparation method according to an embodiment of the present invention is characterized in including polymerizing a conjugated diene-based monomer in the presence of a catalyst composition including a lanthanide rare earth element-containing compound in a hydrocarbon solvent to prepare an active polymer which is combined with an organometal (step 1); and reacting the active polymer with a modifier represented by the following Formula 1 (step 2):

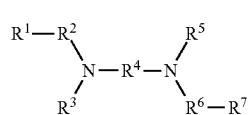

[Formula 1]

in Formula 1,
$R^1$— is —COOR$^8$,
$R^2$ and $R^6$ are each independently a divalent hydrocarbon group of 2 to 20 carbon atoms,
$R^3$ and $R^5$ are each independently —SiR$^9$R$^{10}$R$^{11}$,
$R^4$ is a divalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms,
$R^7$ is —COOR$^{12}$,
where $R^8$ and $R^{12}$ are each independently a monovalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms, and
$R^9$ to $R^{11}$ are each independently a monovalent hydrocarbon group of 1 to 20 carbon atoms, or a monovalent hydrocarbon group of 1 to 20 carbon atoms including one or more heteroatoms selected from the group consisting of N, S and O.

A particular modifier represented by Formula 1 may be the same as described above.

Step 1 is a step for preparing an active polymer which is combined with an organometal, using a catalyst composition including a lanthanide rare earth element-containing compound, and may be performed by polymerizing a conjugated diene-based monomer in the presence of the catalyst composition in a hydrocarbon solvent.

The conjugated diene-based monomer is not specifically limited, but may be, for example, one or more selected from the group consisting of 1,3-butadiene, 2,3-dimethyl-1,3-butadiene, piperylene, 3-butyl-1,3-octadiene, isoprene and 2-phenyl-1,3-butadiene.

The hydrocarbon solvent is not specifically limited, but may be, for example, one or more selected from the group consisting of n-pentane, n-hexane, n-heptane, isooctane, cyclohexane, toluene, benzene and xylene.

The catalyst composition may be used in an amount such that the lanthanide rare earth element-containing compound is from 0.1 mmol to 0.5 mmol based on total 100 g of the conjugated diene-based monomer, particularly, the lanthanide rare earth element-containing compound is from 0.1 mmol to 0.4 mmol, more particularly, from 0.1 mmol to 0.25 mmol based on total 100 g of the conjugated diene-based monomer.

The lanthanide rare earth element-containing compound is not specifically limited, but may be, for example, one among rare earth metals with atomic number of 57 to 71 such as lanthanum, neodymium, cerium, gadolinium and praseodymium, or a compound of two or more thereof, more particularly, a compound including one or more selected from the group consisting of neodymium, lanthanum and gadolinium.

In addition, the lanthanide rare earth element-containing compound may include rare earth element-containing carboxylates (for example, neodymium acetate, neodymium acrylate, neodymium methacrylate, neodymium gluconate, neodymium citrate, neodymium fumarate, neodymium lactate, neodymium maleate, neodymium oxalate, neodymium 2-ethylhexanoate, neodymium neodecanoate, etc.); organic phosphates (for example, neodymium dibutyl phosphate, neodymium dipentyl phosphate, neodymium dihexyl phosphate, neodymium diheptyl phosphate, neodymium dioctyl phosphate, neodymium bis(1-methyl heptyl) phosphate, neodymium bis(2-ethylhexyl) phosphate, neodymium didecyl phosphate, etc.); organic phosphonates (for example, neodymium butyl phosphonate, neodymium pentyl phosphonate, neodymium hexyl phosphonate, neodymium heptyl phosphonate, neodymium octyl phosphonate, neodymium (1-methyl heptyl) phosphonate, neodymium (2-ethylhexyl) phosphonate, neodymium decyl phosphonate, neodymium dodecyl phosphonate, neodymium octadecyl phosphonate, etc.); organic phosphinates (for example, neodymium butyl phosphinate, neodymium pentyl phosphinate, neodymium hexyl phosphinate, neodymium heptyl phosphinate, neodymium octyl phosphinate, neodymium (1-methyl heptyl) phosphinate, neodymium (2-ethylhexyl) phosphinate, etc.); carbamates (for example, neodymium dimethyl carbamate, neodymium diethyl carbamate, neodymium diisopropyl carbamate, neodymium dibutyl carbamate, neodymium dibenzyl carbamate, etc.); dithio carbamates (for example, neodymium dimethyldithio carbamate, neodymium diethyldithio carbamate, neodymium diisopropyl dithio carbamate, neodymium dibutyldithio carbamate, etc.); xanthogenates (for example, neodymium methyl xanthogenate, neodymium ethyl xanthogenate, neodymium isopropyl xanthogenate, neodymium butyl xanthogenate, neodymium benzyl xanthogenate, etc.); ?-diketonates (for example, neodymium acetylacetonate, neodymium trifluoroacetyl acetonate, neodymium hexafluoroacetyl acetonate, neodymium benzoyl acetonate, etc.); alkoxides or phenoxides (for example, neodymium methoxide, neodymium ethoxide, neodymium isopropoxide, neodymium phenoxide, neodymium nonyl phenoxide, etc.); halides or pseudo halides (neodymium fluoride, neodymium chloride, neodymium bromide, neodymium iodide, neodymium cyanide, neodymium cyanate, neodymium thiocyanate, neodymium azide, etc.); oxyhalides (for example, neodymium oxyfluoride, neodymium oxychloride, neodymium oxybromide, etc.); or organic lanthanide rare earth element-containing compounds including one or more rare earth element-carbon bonds (for example, $Cp_3Ln$, $Cp_2LnR$, $CpLnCl_2$, $Cp_2LnCl$, CpLn (cyclooctatetraene), $(C_5Me_5)_2LnR$, $LnR_3$, $Ln(allyl)_3$, $Ln(allyl)_2Cl$, etc., where Ln is a rare earth metal element, and R is a hydrocarbyl group), etc., and may include any one or a mixture of two or more thereof.

Particularly, the lanthanide rare earth element-containing compound may include a neodymium-based compound represented by the following Formula 9:

[Formula 9]

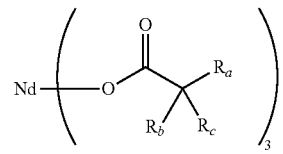

In Formula 9, $R_a$ to $R_c$ may be each independently hydrogen or an alkyl group of 1 to 12 carbon atoms, where $R_a$ to $R_c$ are not hydrogen at the same time.

In particular embodiment, the neodymium-based compound may be one or more selected from the group consisting of $Nd(neodecanoate)_3$, $Nd(2-ethylhexanoate)_3$, $Nd(2,2-diethyl\ decanoate)_3$, $Nd(2,2-dipropyl\ decanoate)_3$, $Nd(2,2-dibutyl\ decanoate)_3$, $Nd(2,2-dihexyl\ decanoate)_3$, $Nd(2,2-dioctyl\ decanoate)_3$, $Nd(2-ethyl-2-propyl\ decanoate)_3$, $Nd(2-ethyl-2-butyl\ decanoate)_3$, $Nd(2-ethyl-2-hexyl\ decanoate)_3$, $Nd(2-propyl-2-butyl\ decanoate)_3$, $Nd(2-propyl-2-hexyl\ decanoate)_3$, $Nd(2-propyl-2-isopropyl\ decanoate)_3$, $Nd(2-butyl-2-hexyl\ decanoate)_3$, $Nd(2-hexyl-2-octyl\ decanoate)_3$, $Nd(2-t-butyl\ decanoate)_3$, $Nd(2,2-diethyl\ octanoate)_3$, $Nd(2,2-dipropyl\ octanoate)_3$, $Nd(2,2-dibutyl\ octanoate)_3$, $Nd(2,2-dihexyl\ octanoate)_3$, $Nd(2-ethyl-2-propyl\ octanoate)_3$, $Nd(2-ethyl-2-hexyl\ octanoate)_3$, $Nd(2,2-diethyl\ nonanoate)_3$, $Nd(2,2-dipropyl\ nonanoate)_3$, $Nd(2,2-dibutyl\ nonanoate)_3$, $Nd(2,2-dihexyl\ nonanoate)_3$, $Nd(2-ethyl-2-propyl\ nonanoate)_3$ and $Nd(2-ethyl-2-hexyl\ nonanoate)_3$.

In another embodiment, considering excellent solubility in a polymerization solvent without fear of oligomerization and conversion ratio to catalytically active species, and consequential excellent improving effect of catalyst activity, the lanthanide rare earth element-containing compound may be a neodymium-based compound, more particularly, Formula 9 where $R_a$ is a linear or branched alkyl group of 4 to 12 carbon atoms, and $R_b$ and $R_c$ are each independently hydrogen or an alkyl group of 2 to 8 carbon atoms, where $R_b$ and $R_c$ are not hydrogen at the same time.

In a more particular embodiment, in Formula 9, $R_a$ may be a linear or branched alkyl group of 6 to 8 carbon atoms, and $R_b$ and $R_c$ may be each independently hydrogen or a linear or branched alkyl group of 2 to 6 carbon atoms, where $R_b$ and $R_c$ may not be hydrogen at the same time, and the particular examples thereof may include one or more selected from the group consisting of $Nd(2,2-diethyl\ decanoate)_3$, $Nd(2,2-dipropyl\ decanoate)_3$, $Nd(2,2-dibutyl\ decanoate)_3$, $Nd(2,2-dihexyl\ decanoate)_3$, $Nd(2,2-dioctyl\ decanoate)_3$, $Nd(2-ethyl-2-propyl\ decanoate)_3$, $Nd(2-ethyl-2-butyl\ decanoate)_3$, $Nd(2-ethyl-2-hexyl\ decanoate)_3$, $Nd(2-propyl-2-butyl\ decanoate)_3$, $Nd(2-propyl-2-hexyl\ decanoate)_3$, $Nd(2-propyl-2-isopropyl\ decanoate)_3$, $Nd(2-butyl-2-hexyl\ decanoate)_3$, $Nd(2-hexyl-2-octyl\ decanoate)_3$, $Nd(2-t-butyl\ decanoate)_3$, $Nd(2,2-diethyl\ octanoate)_3$, $Nd(2,2-dipropyl\ octanoate)_3$, $Nd(2,2-dibutyl\ octanoate)_3$, $Nd(2,2-dihexyl\ octanoate)_3$, $Nd(2-ethyl-2-propyl\ octanoate)_3$, $Nd(2-ethyl-2-hexyl\ octanoate)_3$, $Nd(2,2-diethyl\ nonanoate)_3$, $Nd(2,2-dipropyl\ nonanoate)_3$, $Nd(2,2-dibutyl\ nonanoate)_3$, $Nd(2,2-dihexyl\ nonanoate)_3$, $Nd(2-ethyl-2-propyl\ nonanoate)_3$ and $Nd(2-ethyl-2-hexyl\ nonanoate)_3$, and among them, the neodymium-based compound may be one or more selected from the group consisting of $Nd(2,2-diethyl$ decanoate)$_3$, Nd(2,2-dipropyl decanoate)$_3$, Nd(2,2-dibutyl decanoate)$_3$, Nd(2,2-dihexyl decanoate)$_3$, and Nd(2,2-dioctyl decanoate)$_3$.

More particularly, in Formula 9, $R_a$ may be a linear or branched alkyl group of 6 to 8 carbon atoms, and $R_b$ and $R_c$ may be each independently a linear or branched alkyl group of 2 to 6 carbon atoms.

As described above, the neodymium-based compound represented by Formula 9 includes a carboxylate ligand containing an alkyl group having various lengths of two or more carbon atoms at an α (alpha) position as a substituent, and steric change may be induced around a neodymium central metal to block the tangling among compounds, and as a result, the restraining effect of oligomerization may be achieved. Also, such a neodymium-based compound has high solubility in a polymerization solvent, and the ratio of neodymium positioned at the central part, which has difficulty in conversion into a catalyst active species, is decreased, and thus, a conversion ratio into the catalyst active species is high.

In addition, the lanthanide rare earth element-containing compound according to an embodiment of the present invention may have a solubility of about 4 g or more per 6 g of a non-polar solvent at room temperature (25° C.)

In the present invention, the solubility of the neodymium-based compound means the degree of clear dissolution without generating turbid phenomenon. Through such high solubility, excellent catalyst activity may be attained.

In addition, the lanthanide rare earth element-containing compound according to an embodiment of the present invention may be used as a reaction product type with a Lewis base. Due to the Lewis base, the reaction product may attain improved solubility of the lanthanide rare earth element-containing compound in a solvent and may attain the effect of stable storage for a long time. The Lewis base may be used, for example, in a ratio of 30 mol or less, or 1 to 10 mol per 1 mol of a rare earth element. The Lewis base may be, for example, acetyl acetone, tetrahydrofuran, pyridine, N,N-dimethylformamide, thiophene, diphenyl ether, triethylamine, organophosphorous compounds or monohydric or dihydric alcohols.

Meanwhile, the catalyst composition may further include at least one of (a) an alkylating agent, (b) a halide and (c) a conjugated diene-based monomer together with the lanthanide rare earth element-containing compound.

Hereinafter, (a) the alkylating agent, (b) the halide and (c) the conjugated diene-based monomer will be explained in particular, separately.

(a) Alkylating Agent

The alkylating agent is an organometal compound which is capable of delivering a hydrocarbyl group to another metal, and plays the role of a co-catalyst composition. The alkylating agent may be generally any alkylating agents used for the preparation of a common diene-based polymer, without specific limitation. For example, the alkylating agent may be an organometal compound that is soluble in a polymerization solvent and includes a metal-carbon bond, such as organoaluminum compounds, organomagnesium compounds and organolithium compounds.

Particularly, the organoaluminum compound may include alkyl aluminums such as trimethylaluminum, triethylaluminum, tri-n-propylaluminum, triisopropylaluminum, tri-n-butylaluminum, triisobutylaluminum, tri-t-butylaluminum, tripentylaluminum, trihexylaluminum, tricyclohexylaluminum, and trioctylaluminum; dihydrocarbylaluminum hydrides such as diethylaluminum hydride, di-n-propylaluminum hydride, diisopropylaluminum hydride, di-n-butylaluminum hydride, diisobutylaluminum hydride (DIBAH), di-n-octylaluminum hydride, diphenylaluminum hydride, di-p-tolylaluminum hydride, dibenzylaluminum hydride, phenylethylaluminum hydride, phenyl-n-propylaluminum hydride, phenylisopropylaluminum hydride, phenyl-n-butylaluminum hydride, phenylisobutylaluminum hydride, phenyl-n-octylaluminum hydride, p-tolylethylaluminum hydride, p-tolyl-n-propylaluminum hydride, p-tolylisopropylaluminum hydride, p-tolyl-n-butylaluminum hydride, p-tolylisobutylaluminum hydride, p-tolyl-n-octylaluminum hydride, benzylethylaluminum hydride, benzyl-n-propylaluminum hydride, benzylisopropylaluminum hydride, benzyl-n-butylaluminum hydride, benzylisobutylaluminum hydride and benzyl-n-octylaluminum hydride; hydrocarbylaluminum dihydrides such as ethylaluminum dihydride, n-propylaluminum dihydride, isopropylaluminum dihydride, n-butylaluminum dihydride, isobutylaluminum dihydride, and n-octylaluminum dihydride, or the like. The organomagnesium compound may include alkylmagnesium compounds such as diethylmagnesium, di-n-propylmagnesium, diisopropylmagnesium, dibutylmagnesium, dihexylmagnesium, diphenylmagnesium and dibenzylmagnesium, and the organolithium compound may include alkyl lithium compounds such as n-butyllithium.

In addition, the organoaluminum compound may be aluminoxanes.

The aluminoxane may be prepared by reacting trihydrocarbyl aluminum-based compounds with water, and may particularly be linear aluminoxanes of the following Formula 10a or circular aluminoxanes of the following Formula 10b:

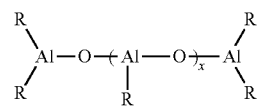

[Formula 10a]

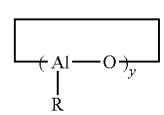

[Formula 10a]

In Formulae 10a and 10b, R is a monovalent organic group which is combined with an aluminum atom via a carbon atom, and may be a hydrocarbyl group, and x and y may be each independently an integer of 1 or more, particularly, an integer of 1 to 100, and more particularly, an integer of 2 to 50.

More particularly, the aluminoxane may be, methylaluminoxane (MAO), modified methylaluminoxane (MAO), ethylaluminoxane, n-propylaluminoxane, isopropylaluminoxane, butylaluminoxane, isobutylaluminoxane, n-pentylaluminoxane, neopentylaluminoxane, n-hexylaluminoxane, n-octylaluminoxane, 2-ethylhexylaluminoxane, cyclohexylaluminoxane, 1-methylcyclopentylaluminoxane, phenylaluminoxane or 2,6-dimethylphenyl aluminoxane, and any one or a mixture of two or more thereof may be used.

In addition, the modified methylaluminoxane is obtained by substituting the methyl group of the methylaluminoxane with a modifier (R), particularly, a hydrocarbon group of 2 to 20 carbon atoms, and particularly, may be a compound represented by the following Formula 11:

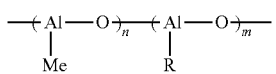

[Formula 11]

In Formula 11, R is the same as defined above, and m and n may be each independently an integer of 2 or more. In addition, in Formula 11, Me represents a methyl group.

Particularly, R in Formula 11 may be a linear or branched alkyl group of 2 to 20 carbon atoms, a cycloalkyl group of 3 to 20 carbon atoms, an alkenyl group of 2 to 20 carbon atoms, a cycloalkenyl group of 3 to 20 carbon atoms, an aryl group of 6 to 20 carbon atoms, an arylalkyl group of 7 to 20 carbon atoms, an alkylaryl group of 7 to 20 carbon atoms, an allyl group, or an alkynyl group of 2 to 20 carbon atoms, and more particularly, may be a linear or branched alkyl group of 2 to 10 carbon atoms such as an ethyl group, an isobutyl group, a hexyl group and an octyl group, and even more particularly, may be an isobutyl group.

More particularly, the modified methylaluminoxane may be obtained by substituting about 50 mol % to 90 mol % of the methyl group of the methylaluminoxane with the hydrocarbon group. If the amount of the substituted hydrocarbon group in the modified methylaluminoxane is in the above-mentioned range, alkylation may be promoted, and catalyst activity may be improved.

Such modified methylaluminoxane may be prepared by a common method, and particularly, may be prepared using trimethylaluminum and an alkylaluminum other than trimethylaluminum. In this case, the alkylaluminum may be triisobutylaluminum, triethylaluminum, trihexylaluminum, or trioctylaluminum, and any one or a mixture of two or more thereof may be used.

In addition, the catalyst composition according to an embodiment of the present invention may include the alkylating agent in a molar ratio of 1 to 200 mol, particularly, 1 to 100 mol, more particularly, 3 to 20 mol with respect to 1 mol of the lanthanide rare earth element-containing compound. If the alkylating agent is included in a molar ratio of greater than 200 mol, the control of catalyst reaction during preparing a polymer is not easy, and the excessive amount of the alkylating agent may induce side reactions.

(b) Halide

Examples of the halide are not specifically limited, but the halide may be a diatomic halogen, an interhalogen compound, a hydrogen halide, an organic halide, a nonmetal halide, a metal halide, or an organometal halide, and any one of them or a mixture of two or more thereof may be used. Among them, considering the improvement of catalyst activity and consequent improving effect of reactivity, the halide may be any one selected from the group consisting of an organic halide, a metal halide and an organometal halide, or a mixture of two or more thereof.

The diatomic halogen may include fluorine, chlorine, bromine, or iodine.

Also, the interhalogen compound may include iodine monochloride, iodine monobromide, iodine trichloride, iodine pentafluoride, iodine monofluoride, iodine trifluoride, etc.

Also, the hydrogen halide may include hydrogen fluoride, hydrogen chloride, hydrogen bromide, or hydrogen iodide.

Also, the organic halide may include t-butyl chloride (t-BuCl), t-butyl bromide, allyl chloride, allyl bromide, benzyl chloride, benzyl bromide, chloro-di-phenylmethane, bromo-di-phenylmethane, triphenylmethyl chloride, triphenylmethyl bromide, benzylidene chloride, benzylidene bromide, methyltrichlorosilane, phenyltrichlorosilane, dimethyldichlorosilane, diphenyldichlorosilane, trimethylchlorosilane (TMSCl), benzoyl chloride, benzoyl bromide, propionyl chloride, propionyl bromide, methyl chloroformate, methyl bromoformate, iodomethane, diiodomethane, triiodomethane (also referred to as "iodoform"), tetraiodomethane, 1-iodopropane, 2-iodopropane, 1,3-diiodopropane, t-butyl iodide, 2,2-dimethyl-1-iodopropane (also referred to as "neopentyl iodide"), allyl iodide, iodobenzene, benzyl iodide, diphenylmethyl iodide, triphenylmethyl iodide, benzylidene iodide (also referred to as "benzal iodide"), trimethylsilyl iodide, triethylsilyl iodide, triphenylsilyl iodide, dimethyldiiodosilane, diethyldiiodosilane, diphenyldiiodosilane, methyltriiodosilane, ethyltriiodosilane, phenyltriiodosilane, benzoyl iodide, propionyl iodide, methyl iodoformate, or the like.

In addition, the nonmetal halide may include phosphorus trichloride, phosphorus tribromide, phosphorus pentachloride, phosphorus oxychloride, phosphorus oxybromide, boron trifluoride, boron trichloride, boron tribromide, silicon tetrafluoride, silicon tetrachloride ($SiCl_4$), silicon tetrabromide, arsenic trichloride, arsenic tribromide, selenium tetrachloride, selenium tetrabromide, tellurium tetrachloride, tellurium tetrabromide, silicon tetraiodide, arsenic triiodide, tellurium tetraiodide, boron triiodide, phosphor triiodide, phosphor oxyiodide, selenium tetraiodide, or the like.

Also, the metal halide may include tin tetrachloride, tin tetrabromide, aluminum trichloride, aluminum tribromide, antimony trichloride, antimony pentachloride, antimony tribromide, aluminum tribromide, gallium trichloride, gallium tribromide, gallium trifluoride, indium trichloride, indium tribromide, indium trifluoride, titanium tetrachloride, titanium tetrabromide, zinc dichloride, zinc dibromide, zinc difluoride, aluminum triiodide, gallium triiodide, indium triiodide, titanium tetraiodide, zinc diiodide, germanium tetraiodide, tin tetraiodide, tin diiodide, antimony triiodide or magnesium diiodide.

Also, the organometal halide may include dimethylaluminum chloride, diethylaluminum chloride, dimethylaluminum bromide, diethylaluminum bromide, dimethylaluminum fluoride, diethylaluminum fluoride, methylaluminum dichloride, ethylaluminum dichloride, methylaluminum dibromide, ethylaluminum dibromide, methylaluminum difluoride, ethylaluminum difluoride, methylaluminum sesquichloride, ethylaluminum sesquichloride (EASC), isobutylaluminum sesquichloride, methylmagnesium chloride, methylmagnesium bromide, ethylmagnesium chloride, ethylmagnesium bromide, n-butylmagnesium chloride, n-butylmagnesium bromide, phenylmagnesium chloride, phenylmagnesium bromide, benzylmagnesium chloride, trimethyltin chloride, trimethyltin bromide, triethyltin chloride, triethyltin bromide, di-t-butyltin dichloride, di-t-butyltin dibromide, di-n-butyltin dichloride, di-n-butyltin dibromide, tri-n-butyltin chloride, tri-n-butyltin bromide, methylmagnesium iodide, dimethylaluminum iodide, diethylaluminum iodide, di-n-butylaluminum iodide, diisobutylaluminum iodide, di-n-octylaluminum iodide, methylaluminum diiodide, ethylaluminum diiodide, n-butylaluminum diiodide, isobutylaluminum diiodide, methylaluminum sesquiiodide, ethylaluminum sesquiiodide, isobutylaluminum sesquiiodide, ethylmagnesium iodide, n-butylmagnesium iodide, isobutylmagnesium iodide, phenylmagnesium iodide, benzylmagnesium iodide, trimethyltin iodide, triethyltin iodide, tri-n-butyltin iodide, di-n-butyltin diiodide, di-t-butyltin diiodide, or the like.

In addition, the catalyst composition according to an embodiment of the present invention may include the halide in a molar ratio of 1 mol to 20 mol, more particularly, 1 mol to 5 mol, more particularly, 2 mol to 3 mol with respect to 1 mol of the lanthanide rare earth element-containing compound. If the molar ratio of the halide is greater than 20 mol, the control of catalyst reaction is not easy, and it is apprehended that the excessive amount of the halide may induce side reactions.

In addition, the catalyst composition for preparing the conjugated diene polymer according to an embodiment of the present invention may include a non-coordinating anion-containing compound or a non-coordinating anion precursor compound instead of the halide or together with the halide.

Particularly, in the compound containing the non-coordinating anion, the non-coordinating anion may be an anion not forming a coordination bond with the active center of a catalyst system due to steric hindrance, and having a sterically large volume, and may be a tetraarylborate anion or a tetraarylborate fluoride anion. In addition, the compound containing the non-coordinating anion may include together with the non-coordinating anion, a carbonium cation such as a triaryl carbonium cation; an ammonium cation such as N,N-dialkyl anilinium cation, or a counter cation such as a phosphonium cation. More particularly, the compound containing the non-coordinating anion may be triphenylcarbonium tetrakis(pentafluorophenyl)borate, N,N-dimethylanilinium tetrakis(pentafluorophenyl)borate, triphenylcarbonium tetrakis[3,5-bis(trifluoromethyl) phenyl]borate, N,N-dimethylanilinium tetrakis[3,5-bis(trifluoromethyl)phenyl]borate, or the like.

In addition, as the non-coordinating anion precursor, triaryl boron compound ($BE_3$, where E is a strongly electron withdrawing aryl group such as a pentafluorophenyl group and a 3,5-bis(trifluoromethyl) phenyl group) may be used as a compound capable of forming a non-coordinating anion under reaction conditions.

(c) Conjugated Diene-Based Monomer

Also, the catalyst composition may further include a conjugated diene-based monomer and may be used as a preforming catalyst composition type which is obtained by mixing a portion of the conjugated diene-based monomer used in polymerization reaction with a catalyst composition for polymerization and pre-polymerizing. Then, the activity of the catalyst composition may be improved and the conjugated diene-based polymer thus prepared may be stabilized.

In the present invention, the meaning of the "preforming" is as follows. If diisobutylaluminum hydride (DIBAH), etc. is included in a catalyst composition including a lanthanide rare earth element-containing compound, an alkylating agent and a halide, i.e., in a catalyst system, a small amount of a conjugated diene-based monomer such as 1,3-butadiene may be added to decrease the production possibility of diverse active species of the catalyst composition together with the DIBAH, and pre-polymerization may be performed in a catalyst composition system with the addition of 1,3-butadiene. In addition, the "premix" may mean a homogeneously mixed state of each compound without forming a polymer in a catalyst composition system.

In this case, the conjugated diene-based monomer used for the preparation of the catalyst composition may be a partial amount within the total amount range of the conjugated diene-based monomer used in the polymerization reaction, and for example, may be 1 mol to 100 mol, particularly, 10 mol to 50 mol, or 20 mol to 50 mol with respect to 1 mol of the lanthanide rare earth element-containing compound.

The catalyst composition according to an embodiment of the present invention may be prepared by mixing the above-mentioned lanthanide rare earth element-containing compound, the alkylating agent, the halide and at least one conjugated diene-based monomer, particularly, the lanthanide rare earth element-containing compound, the alkylating agent and the halide, and selectively the conjugated diene-based monomer, one by one in an organic solvent. In this case, the organic solvent may be a non-polar solvent having no reactivity with the components constituting the catalyst. Particularly, linear, branched or cyclic aliphatic hydrocarbon of 5 to 20 carbon atoms such as n-pentane, n-hexane, n-heptane, n-octane, n-nonane, n-decane, isopentane, isohexane, isooctane, 2,2-dimethylbutane, cyclopentane, cyclohexane, methylcyclopentane and methylcyclohexane; a mixture solvent of aliphatic hydrocarbon of 5 to 20 carbon atoms such as petroleum ether, petroleum spirits, and kerosene; or an aromatic hydrocarbon-based solvent such as benzene, toluene, ethylbenzene, and xylene, and any one or a mixture of two or more thereof may be used. More particularly, the non-polar solvent may be the above-mentioned linear, branched or cyclic aliphatic hydrocarbon of 5 to 20 carbon atoms or a mixture solvent of the aliphatic hydrocarbons, more particularly, n-hexane, cyclohexane, or a mixture thereof.

In addition, the organic solvent may be appropriately selected according to the kind of the materials constituting the catalyst composition, specifically, the alkylating agent.

In particular, in case where an alkylaluminoxane such as methylaluminoxane (MAO) and ethylaluminoxane is used as the alkylating agent, it is not easily dissolved in an aliphatic hydrocarbon-based solvent, and an aromatic hydrocarbon-based solvent may be appropriately used.

In addition, in case where modified methylaluminoxane is used as the alkylating agent, an aliphatic hydrocarbon-based solvent may be appropriately used. In this case, a single solvent system may be achieved together with an aliphatic hydrocarbon-based solvent such as hexane, which is mainly used as a polymerization solvent, and the polymerization reaction may become more favorable. In addition, the aliphatic hydrocarbon-based solvent may promote catalyst activity, and reactivity may be further improved due to such catalyst activity.

In addition, the organic solvent may be used in a molar ratio of 20 to 20,000 mol, more particularly, 100 mol to 1,000 mol with respect to 1 mol of the lanthanide rare earth element-containing compound.

Meanwhile, the polymerization in step 1 may be performed by coordination anion polymerization or radical polymerization, particularly, bulk polymerization, solution polymerization, suspension polymerization or emulsion polymerization, more particularly, solution polymerization.

In addition, the polymerization may be performed by any method among a batch type and a continuous type. Particularly, the polymerization in step 1 may be performed by injecting a conjugated diene-based monomer to the catalyst composition in an organic solvent and performing reaction.

Here, the organic solvent may be additionally added to the amount of the organic solvent used for preparing the catalyst composition, and particular kinds may be the same as described above. In addition, the concentration of the monomer when using the organic solvent may be from 3 wt % to 80 wt %, or from 10 wt % to 30 wt %.

In addition, the polymerization may further use an additive such as a reaction quenching agent for finishing polymerization reaction such as polyoxyethylene glycol phosphate; and an antioxidant such as 2,6-di-t-butylparacresol.

Besides, additives for favorable solution polymerization, particularly, additives such as a chelating agent, a dispersant, a pH controller, a deoxidizing agent and an oxygen scavenger may be selectively further used.

In addition, the polymerization may be a polymerization with heating, an isothermal polymerization, or a polymerization at a constant temperature (adiabatic polymerization).

Here, the polymerization at a constant temperature means a polymerization method including a step of polymerizing using self-generated heat of reaction without optionally applying heat after adding an organometal compound, and the polymerization with heating means a polymerization method including injecting the organometal compound and then, increasing the temperature by optionally applying heat. The isothermal polymerization means a polymerization method by which the temperature of a polymer is kept constant by increasing heat by applying heat or taking heat after adding the organometal compound.

The polymerization may be performed in a temperature range of −20° C. to 200° C., particularly, 20° C. to 150° C., more particularly, 10° C. to 120° C. for 15 minutes to 3 hours. If the temperature during polymerization is greater than 200° C., it is apprehended that the polymerization reaction may be insufficiently controlled, and the cis-1,4 bond content of the diene-based polymer thus produced may decrease, and if the temperature is less than −20° C., it is apprehended that a polymerization reaction rate and efficiency may decrease.

Step 2 is a step of reacting the active polymer and the modifier represented by Formula 1 to prepare a modified conjugated diene-based polymer.

The modifier represented by Formula 1 may be the same as described above, and one kind or two or more kinds thereof may be mixed and used in the reaction.

The modifier represented by Formula 1 may be used in 0.5 mol to 20 mol with respect to 1 mol of the lanthanide rare earth element-containing compound in the catalyst composition. Particularly, the modifier represented by Formula 1 may be used in 1 mol to 10 mol with respect to 1 mol of the lanthanide rare earth element-containing compound in the catalyst composition. If the modifier is used in an amount in the above-mentioned ratio range, modification reaction with optimized performance may be performed, and a conjugated diene-based polymer with a high modification ratio may be obtained.

The reaction in step 2 is modification reaction for introducing a functional group into a polymer, and may be performed at 0° C. to 90° C. for 1 minute to 5 hours.

In addition, the preparation method of the modified conjugated diene-based polymer according to an embodiment of the present invention may be performed by a batch type or a continuous polymerization method including one or more kinds of reactors.

After finishing the modification reaction, the polymerization reaction may be quenched by adding an isopropanol solution of 2,6-di-t-butyl-p-cresol, etc. to a polymerization reaction system.

The preparation method according to an embodiment of the present invention may further include one or more steps among recovering and drying solvents and an unreacted monomer after step 2, as necessary.

Particularly, as a subsequent process after quenching the polymerization reaction, desolvation treatment such as steam stripping lowering the partial pressure of a solvent via the supply of vapor, or a vacuum drying treatment may be performed to obtain a modified conjugated diene-based polymer. In addition, in the reaction product obtained as the result of the modification reaction, an unmodified active polymer may be included together with the modified conjugated diene-based polymer.

In addition, in the subsequent process supplying vapor, a step of hydrolyzing $R^3$ and $R^5$ substituents, which are combined with an amine group among the functional groups derived from the modifier represented by Formula 1, and separating from amine groups to produce two secondary amine groups in the modified conjugated diene-based polymer, may be included. In this case, by forming two secondary amine groups, affinity with a filler such as carbon black may be improved to an excellent degree.

Further, there is provided in the present invention a rubber composition including the modified conjugated diene-based polymer and a molded article manufactured from the rubber composition.

The rubber composition according to an embodiment of the present invention may include the modified conjugated diene-based polymer in an amount of 0.1 wt % to 100 wt %, particularly, 10 wt % to 100 wt %, more particularly, 20 wt % to 90 wt %. If the amount of the modified conjugated diene-based polymer is less than 0.1 wt %, the improving effects of the abrasion resistance and crack resistance of the molded article, for example, a tire may become insignificant.

In addition, the rubber composition may further include other rubber component in addition to the modified conjugated diene-based polymer as necessary, and in this case, the rubber component may be included in an amount of 90 wt % or less with respect to the total weight of the rubber composition. Particularly, the rubber composition may include the rubber component in an amount of 1 part by weight to 900 parts by weight with respect to 100 parts by weight of the modified conjugated diene-based copolymer.

The rubber component may be natural rubber or synthetic rubber, for example, natural rubber (NR) including cis-1,4-polyisoprene; modified natural rubber which is obtained by modifying or purifying common natural rubber, such as epoxidized natural rubber (ENR), deproteinized natural rubber (DPNR), and hydrogenated natural rubber; and synthetic rubber such as styrene-butadiene copolymer (SBR), polybutadiene (BR), polyisoprene (IR), butyl rubber (IIR), ethylene-propylene copolymer, polyisobutylene-co-isoprene, neoprene, poly(ethylene-co-propylene), poly(styrene-co-butadiene), poly(styrene-co-isoprene), poly(styrene-co-isoprene-co-butadiene), poly(isoprene-co-butadiene), poly(ethylene-co-propylene-co-diene), polysulfide rubber, acryl rubber, urethane rubber, silicone rubber, epichlorohydrin rubber, and halogenated butyl rubber, and any one thereof or a mixture of two or more thereof may be used.

In addition, the rubber composition may include 0.1 parts by weight to 150 parts by weight of a filler with respect to 100 parts by weight of the modified conjugated diene-based polymer, and the filler may be a silica-based filler, carbon black or a combination thereof. Particularly, the filler may be carbon black.

The carbon black filler is not specifically limited but may have a nitrogen adsorption specific surface area of (measured based on N2SA, JIS K 6217-2:2001), for example, 20 $m^2/g$ to 250 $m^2/g$. Also, the carbon black may have a dibutylphthalate oil absorption amount (DBP) of 80 cc/100 g to 200 cc/100 g. If the nitrogen adsorption specific surface area of the carbon black is greater than 250 $m^2/g$, the processability of a rubber composition may be deteriorated, and if the nitrogen adsorption specific surface area is less than 20 $m^2/g$, reinforcing performance by the carbon black may be insignificant. In addition, if the DBP oil absorption amount of the carbon black is greater than 200 cc/100 g, the processability of the rubber composition may be deteriorated, and if the DBP oil absorption amount is less than 80 cc/100 g, reinforcing performance by the carbon black may be insignificant.

In addition, the silica is not specifically limited, and may include, for example, wet silica (hydrated silicate), dry silica (anhydrous silicate), calcium silicate, aluminum silicate or colloid silica. Particularly, the silica may be wet silica which has the most remarkable compatibility effect of the improving effect of destruction characteristics and wet grip. In addition, the silica may have nitrogen absorption specific surface area (nitrogen surface area per gram, N2SA) of 120 $m^2/g$ to 180 $m^2/g$, and cetyl trimethyl ammonium bromide (CTAB) absorption specific surface area of 100 $m^2/g$ to 200 $m^2/g$. If the nitrogen absorption specific surface area is less than 120 $m^2/g$, the reinforcing performance due to silica may be deteriorated, and if the nitrogen absorption specific surface area is greater than 180 $m^2/g$, the processability of the rubber composition may be deteriorated. In addition, if the CTAB absorption specific surface area of the silica is less than 100 $m^2/g$, the reinforcing performance by the silica filler may be deteriorated, and if the CTAB absorption specific surface area is greater than 200 $m^2/g$, the processability of the rubber composition may be deteriorated.

Meanwhile, if the silica is used as the filler, a silane coupling agent may be used together for the improvement of reinforcing and low exothermic properties.

The silane coupling agent may particularly include bis(3-triethoxysilylpropyl)tetrasulfide, bis(3-triethoxysilylpropyl)trisulfide, bis(3-triethoxysilylpropyl)disulfide, bis(2-triethoxysilylethyl)tetrasulfide, bis(3-trimethoxysilylpropyl)tetrasulfide, bis(2-trimethoxysilylethyl)tetrasulfide, 3-mercaptopropyltrimethoxysilane, 3-mercaptopropyltriethoxysilane, 2-mercaptoethyltrimethoxysilane, 2-mercaptoethyltriethoxysilane, 3-trimethoxysilylpropyl-N,N-dimethylthiocarbamoyltetrasulfide, 3-triethoxysilylpropyl-N,N-dimethylthiocarbamoyltetrasulfide, 2-triethoxysilylethyl-N,N-dimethylthiocarbamoyltetrasulfide, 3-trimethoxysilylpropylbenzothiazolyltetrasulfide, 3-triethoxysilylpropylbenzolyltetrasulfide, 3-triethoxysilylpropylmethacrylatemonosulfide, 3-trimethoxysilylpropylmethacrylatemonosulfide, bis(3-diethoxymethylsilylpropyl)tetrasulfide, 3-mercaptopropyldimethoxymethylsilane, dimethoxymethylsilylpropyl-N,N-dimethylthiocarbamoyltetrasulfide, or dimethoxymethylsilylpropylbenzothiazolyltetrasulfide, and any one among them or a mixture of two or more thereof may be used. More particularly, the silane coupling agent may be bis(3-triethoxysilylpropyl) polysulfide or 3-trimethoxysilylpropylbenzothiazyltetrasulfide in consideration of the improving effect of reinforcing properties.

In addition, in the rubber composition according to an embodiment of the present invention, since a modified conjugated diene-based polymer introducing a functional group having high affinity with a filler around an active part is used as a rubber component, the compounding amount of the silane coupling agent may be smaller than a commonly used amount. Particularly, the silane coupling agent may be used in an amount of 1 part by weight to 20 parts by weight with respect to 100 parts by weight of the filler. If used in this range, the effects as a silane coupling agent may be sufficiently shown and the gelation of the rubber component may be prevented. More particularly, the silane coupling agent may be used in an amount of 5 parts by weight to 15 parts by weight with respect to 100 parts by weight of silica.

In addition, the rubber composition according to an embodiment of the present invention may be sulfur crosslinkable, and so may further include a vulcanizing agent.

The vulcanizing agent may be particularly a sulfur powder and may be included in an amount of 0.1 parts by weight to 10 parts by weight with respect to 100 parts by weight of the rubber component. With the amount used in the above range, elasticity and strength required for a vulcanized rubber composition may be secured, and at the same time, a low fuel consumption ratio may be attained.

In addition, the rubber composition according to an embodiment of the present invention may further include various additives used in a common rubber industry in addition to the above components, particularly, a vulcanization accelerator, a process oil, a plasticizer, an antiaging agent, a scorch preventing agent, a zinc white, stearic acid, a thermosetting resin, a thermoplastic resin, or the like.

The vulcanization accelerator is not specifically limited, and may particularly include thiazole-based compounds such as 2-mercaptobenzothiazole (M), dibenzothiazyldisulfide (DM), and N-cyclohexyl-2-benzothiazylsulfenamide (CZ), or guanidine-based compounds such as diphenylguanidine (DPG). The vulcanization accelerator may be included in an amount of 0.1 parts by weight to 5 parts by weight with respect to 100 parts by weight of the rubber component.

In addition, the process oil acts as a softener in a rubber composition and may particularly include a paraffin-based, naphthene-based, or aromatic compound. More particularly, an aromatic process oil may be used in consideration of tensile strength and abrasion resistance, and a naphthene-based or paraffin-based process oil may be used in consideration of hysteresis loss and properties at low temperature. The process oil may be included in an amount of 100 parts by weight or less with respect to 100 parts by weight of the rubber component. With the above-described amount in the range, the deterioration of tensile strength and low exothermic properties (low fuel consumption ratio) of a vulcanized rubber may be prevented.

In addition, the antiaging agent may particularly include N-isopropyl-N'-phenyl-p-phenylenediamine, N-(1,3-dimethylbutyl)-N'-phenyl-p-phenylenediamine, 6-ethoxy-2,2,4-trimethyl-1,2-dihydroquinoline, or a condensate of diphenylamine and acetone at a high temperature. The antiaging agent may be used in an amount of 0.1 parts by weight to 6 parts by weight with respect to 100 parts by weight of the rubber component.

The rubber composition according to an embodiment of the present invention may be obtained by mulling using a mulling apparatus such as a banbury mixer, a roll, and an internal mixer according to a mixing prescription. In addition, a rubber composition having low exothermic properties and excellent abrasion resistance may be obtained by a vulcanization process after a molding process.

Therefore, the rubber composition may be useful to the manufacture of each member of a tire such as a tire tread, an under tread, a side wall, a carcass coating rubber, a belt coating rubber, a bead filler, a chafer, and a bead coating rubber, or to the manufacture of rubber products in various industries such as a vibration-proof rubber, a belt conveyor, and a hose.

The molded article manufactured by using the rubber composition may include a tire or a tire tread.

Hereinafter, the present invention will be explained in particular referring to embodiments and experimental embodiments. However, the embodiments and experimental embodiments below are only for illustrating the present invention, and the scope of the present invention is not limited thereto.

Preparation Example 1

1) Preparation of Compound Represented by Formula 2-1

To a 1 L round-bottom flask, 46.5 g (400 mmol) of hexamethylenediamine, and 88.2 g (880 mmol, 2.2 eq) of ethyl acrylate were slowly added. Then, reaction was performed by stirring at room temperature for 12 hours. After checking the complete consumption of hexamethylenediamine, the reaction was finished, and solvents were removed under a reduced pressure. After that, the resultant product was filtered via a celite pad using 500 ml of n-hexane and concentrated to obtain 120.2 g (yield 95%) of a compound represented by Formula 2-1 below. $^1$H nuclear magnetic resonance spectroscopic data of the compound represented by Formula 2-1 thus obtained are as follows.

[Formula 2-1]

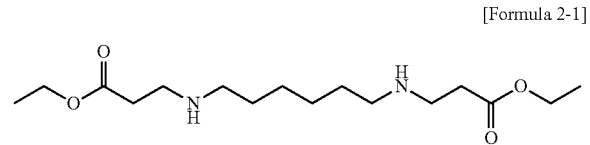 [SMILES: CCOC(=O)CCNCCCCCCNCCC(=O)OCC]

$^1$H-NMR (500 MHz, CDCl$_3$) 4.14 (4H, q), 2.86 (4H, t), 2.67 (2H, td, J=7.0 Hz, 3.5 Hz), 2.59 (2H, t), 2.50 (2H, t), 1.50 (4H, m), 1.33 (4H, m), 1.25 (3H, t)

2) Preparation of Compound Represented by Formula 2

To a 2 L round-bottom flask, 120.2 g (380 mmol) of the compound represented by Formula 2-1 and prepared in 1) above was added, 570 ml of dichloromethane was added, and 115.3 g (1.14 mol, 3.0 eq) of triethylamine was added. Then, the reaction flask was cooled to 0° C. and 94.9 g (873.7 mmol, 2.3 eq) of chlorotrimethylsilane was slowly added, followed by reacting for 12 hours while elevating the reaction temperature to room temperature. After that, the reaction was finished, and solvents were removed under a reduced pressure. The remaining organic material was dissolved in 800 ml of n-hexane, washed three times with 150 ml of acetonitrile, filtered using a celite pad, and concentrated to obtain 138.2 g (yield 79%) of a compound represented by Formula 2 below. $^1$H nuclear magnetic resonance spectroscopic data of the compound represented by Formula 2 thus obtained are as follows.

[Formula 2]

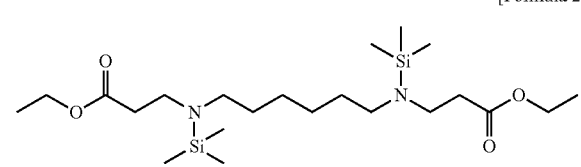

$^1$H-NMR (500 MHz, CDCl$_3$) 4.09 (4H, q), 3.03 (4H, t), 2.64 (2H, t), 2.35 (2H, t), 1.34 (4H, m), 1.23 (6H, t), 1.17 (4H, m), 0.04 (18H, s)

Preparation Example 2

1) Preparation of Compound Represented by Formula 3-1

To a 1 L round-bottom flask, 29.6 g (400 mmol) of 1,3-diaminopropane, and 88.2 g (880 mmol, 2.2 eq) of ethyl acrylate were slowly added. Then, reaction was performed by stirring at room temperature for 12 hours. After checking the complete consumption of 1,3-diaminopropane, the reaction was finished, and solvents were removed under a reduced pressure. After that, the resultant product was filtered via a celite pad using 500 ml of n-hexane and concentrated to obtain 104.2 g (yield 95%) of a compound represented by Formula 3-1 below. $^1$H nuclear magnetic resonance spectroscopic data of the compound represented by Formula 3-1 thus obtained are as follows.

[Formula 3-1]

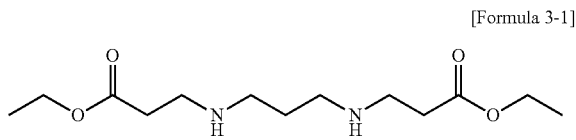 [SMILES: CCOC(=O)CCNCCCNCCC(=O)OCC]

$^1$H-NMR (500 MHz, CDCl$_3$) 4.14 (4H, q), 2.86 (4H, t), 2.59 (4H, t), 2.50 (4H, t), 1.50 (2H, m), 1.25 (6H, t)

2) Preparation of Compound Represented by Formula 3

To a 2 L round-bottom flask, 120.2 g (380 mmol) of the compound represented by Formula 3-1 and prepared in 1) above was added, 570 ml of dichloromethane was added, and 115.3 g (1.14 mol, 3.0 eq) of triethylamine was added. Then, the reaction flask was cooled to 0° C. and 94.9 g (873.7 mmol, 2.3 eq) of chlorotrimethylsilane was slowly added, followed by reacting for 12 hours while elevating the reaction temperature to room temperature. After that, the reaction was finished, and solvents were removed under a reduced pressure. The remaining organic material was dissolved in 800 ml of n-hexane, washed three times with 150 ml of acetonitrile, filtered using a celite pad, and concentrated to obtain 125.99 g (yield 79%) of a compound represented by Formula 3 below. $^1$H nuclear magnetic resonance spectroscopic data of the compound represented by Formula 3 thus obtained are as follows.

[Formula 3]

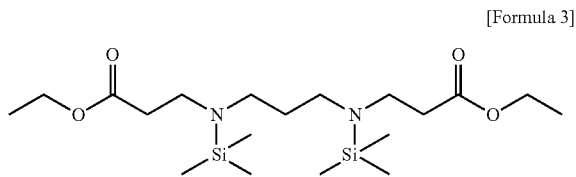 [SMILES: CCOC(=O)CCN(CCCN(CCC(=O)OCC)[Si](C)(C)C)[Si](C)(C)C]

$^1$H-NMR (500 MHz, CDCl$_3$) 4.09 (4H, q), 3.03 (4H, t), 2.64 (4H, t), 2.35 (4H, t), 1.34 (2H, m), 0.08 (18H, s)

Comparative Preparation Example 1

1) Preparation of Compound Represented by Formula 2-1

To a 1 L round-bottom flask, 46.5 g (400 mmol) of hexamethylenediamine, and 88.2 g (880 mmol, 2.2 eq) of ethyl acrylate were slowly added. Then, reaction was performed by stirring at room temperature for 12 hours. After checking the complete consumption of hexamethylenediamine, the reaction was finished, and solvents were removed under a reduced pressure. After that, the resultant product was filtered via a celite pad using 500 ml of n-hexane and concentrated to obtain 120.2 g (yield 95%) of a compound represented by Formula 2-1 below. ¹H nuclear magnetic resonance spectroscopic data of the compound represented by Formula 2-1 thus obtained are as follows.

[Formula 2-1]

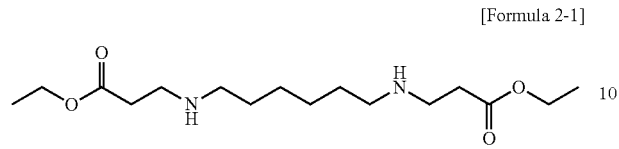

¹H-NMR (500 MHz, CDCl₃) 4.14 (4H, q), 2.86 (4H, t), 2.67 (2H, td, J=7.0 Hz, 3.5 Hz), 2.59 (2H, t), 2.50 (2H, t), 1.50 (4H, m), 1.33 (4H, m), 1.25 (3H, t)

2) Preparation of Compound Represented by Formula 12

To a 2 L round-bottom flask, 120.2 g (380 mmol) of the compound represented by Formula 2-1 and prepared in 1) above was added, 570 ml of dichloromethane was added, and 115.3 g (1.14 mol, 3.0 eq) of triethylamine was added. Then, the reaction flask was cooled to 0° C. and 118.61 g (835.7 mmol, 2.3 eq) of iodomethane was slowly added, followed by reacting for 12 hours while elevating the reaction temperature to room temperature. After that, the reaction was finished, and solvents were removed under a reduced pressure. The remaining organic material was dissolved in 800 ml of n-hexane, washed three times with 150 ml of acetonitrile, filtered using a celite pad, and concentrated to obtain 73.3 g (yield 56%) of a compound represented by Formula 12 below. ¹H nuclear magnetic resonance spectroscopic data of the compound represented by Formula 12 thus obtained are as follows.

[Formula 12]

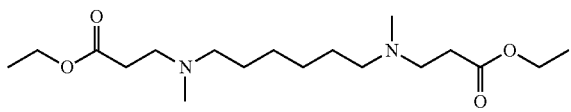

1H-NMR (500 MHz, CDCl₃) 4.09 (4H, q), 3.03 (4H, t), 2.64 (2H, t), 2.35 (6H, s), 1.50-1.33 (8H, m), 1.23 (6H, t)

Comparative Preparation Example 2

To a 1 L round-bottom flask, 46.5 g (400 mmol) of hexamethylenediamine, and 176.27 g (1.76 mol, 4.4 eq) of ethyl acrylate were slowly added. Then, reaction was performed by stirring at room temperature for 12 hours. After checking the complete consumption of hexamethylenediamine, the reaction was finished, and solvents were removed under a reduced pressure. After that, the resultant product was filtered via a celite pad using 500 ml of n-hexane and concentrated to obtain 181.94 g (yield 88%) of a compound represented by Formula 13 below. ¹H nuclear magnetic resonance spectroscopic data of the compound represented by Formula 13 thus obtained are as follows.

[Formula 13]

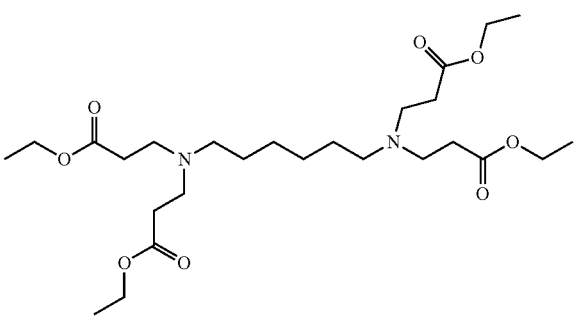

1H-NMR (500 MHz, CDCl₃) 4.14 (8H, q), 2.86 (8H, t), 2.67 (4H, t), 1.50-1.33 (8H, m), 1.25 (12H, t)

Example 1

To a 20 L autoclave reactor, 900 g of 1,3-butadiene and 6.6 kg of n-hexane were added, and the internal temperature of the reactor was elevated to 70° C. A catalyst composition which was prepared by reacting a hexane solution in which 0.10 mmol of a neodymium compound was dissolved, with 0.89 mmol of diisobutylaluminum hydride (DIBAH), 0.24 mmol of diethylaluminum chloride, and 3.3 mmol of 1,3-butadiene, was added to the reactor, and polymerization was performed for 60 minutes. After adding a hexane solution including 0.23 mmol of the compound represented by Formula 2 and prepared in Preparation Example 1 was added thereto, and a modification reaction was performed at 70° C. for 30 minutes. Then, a hexane solution including 1.0 g of a polymerization terminator and 33 g of a solution obtained by dissolving 30 wt % of WINGSTAY (Eliokem SAS, France) antioxidant in hexane, was added. Then, the polymer thus obtained was put in hot water heated by steam and stirred to remove solvents, and roll drying was performed to remove remaining solvent and water to prepare a modified butadiene polymer.

Example 2

A modified butadiene polymer was prepared by performing the same method as in Example 1 except for adding a hexane solution including 0.23 mmol of the compound represented by Formula 3 of Preparation Example 2 instead of the compound represented by Formula 2, which was prepared in Preparation Example 1.

Comparative Example 1

To a 20 L autoclave reactor, 900 g of 1,3-butadiene and 6.6 kg of n-hexane were added, and the internal temperature of the reactor was elevated to 70° C. A catalyst composition which was prepared by reacting a hexane solution in which 0.10 mmol of a neodymium compound was dissolved, with 0.89 mmol of diisobutylaluminum hydride (DIBAH), 0.24 mmol of diethylaluminum chloride, and 3.3 mmol of 1,3-butadiene, was added to the reactor, and polymerization was performed for 60 minutes. After that, a hexane solution including 1 g of a polymerization terminator and 33 g of a solution obtained by dissolving 30 wt % of WINGSTAY (Eliokem SAS, France) antioxidant in hexane, was added. The resultant polymer thus obtained was put in hot water heated by steam and stirred to remove solvents, and roll drying was performed to remove remaining solvent and water to prepare a butadiene polymer.

Comparative Example 2

To a 20 L autoclave reactor, 900 g of 1,3-butadiene and 6.6 kg of n-hexane were added, and the internal temperature of the reactor was elevated to 70° C. A catalyst composition which was prepared by reacting a hexane solution in which 0.10 mmol of a neodymium compound was dissolved, with 0.89 mmol of diisobutylaluminum hydride (DIBAH), 0.24 mmol of diethylaluminum chloride, and 3.3 mmol of 1,3-butadiene, was added to the reactor, and polymerization was performed for 60 minutes. After adding a hexane solution including 0.23 mmol of the compound represented by Formula 12 and prepared in Comparative Preparation Example 1 was added thereto, and a modification reaction was performed at 70° C. for 30 minutes. Then, a hexane solution including 1.0 g of a polymerization terminator and 33 g of a solution obtained by dissolving 30 wt % of WINGSTAY (Eliokem SAS, France) antioxidant in hexane, was added. The resultant polymer thus obtained was put in hot water heated by steam and stirred to remove solvents, and roll drying was performed to remove remaining solvent and water to prepare a modified butadiene polymer.

[Formula 12]

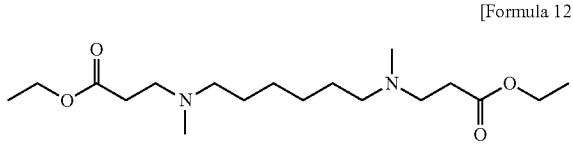

Comparative Example 3

To a 20 L autoclave reactor, 900 g of 1,3-butadiene and 6.6 kg of n-hexane were added, and the internal temperature of the reactor was elevated to 70° C. A catalyst composition which was prepared by reacting a hexane solution in which 0.10 mmol of a neodymium compound was dissolved, with 0.89 mmol of diisobutylaluminum hydride (DIBAH), 0.24 mmol of diethylaluminum chloride, and 3.3 mmol of 1,3-butadiene, was added to the reactor, and polymerization was performed for 60 minutes. After adding a hexane solution including 0.23 mmol of the compound represented by Formula 13 and prepared in Comparative Preparation Example 2 was added thereto, and a modification reaction was performed at 70° C. for 30 minutes. Then, a hexane solution including 1.0 g of a polymerization terminator and 33 g of a solution obtained by dissolving 30 wt % of WINGSTAY (Eliokem SAS, France) antioxidant in hexane, was added. The resultant polymer thus obtained was put in hot water heated by steam and stirred to remove solvents, and roll drying was performed to remove remaining solvent and water to prepare a modified butadiene polymer.

[Formula 13]

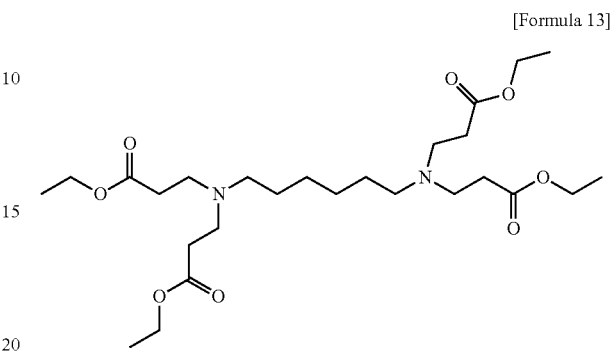

Experimental Example 1

With respect to each of the modified butadiene polymers prepared the Examples and butadiene polymers prepared in Comparative Examples, physical properties were measured by the methods explained below, respectively, and the results are listed in Table 1 below.

1) Weight Average Molecular Weight (Mw), Number Average Molecular Weight (Mn) and Molecular Weight Distribution Each polymer was dissolved in tetrahydrofuran (THF) under 40° C. conditions for 30 minutes, and the resultant solution was loaded on gel permeation chromatography (GPC) and flown. In this case, two columns of PLgel Olexis and one column of PLgel mixed-C (trade name, Polymer Laboratories Co. Ltd.) were used in combination. Also, newly replaced columns were all mixed bed type columns, and polystyrene was used as a GPC standard material.

2) Mooney Viscosity and —S/R Value

The mooney viscosity (MV) was measured by using MV2000E of Monsanto Co. using Large Rotor at the conditions of a rotor speed of 2±0.02 rpm at 100° C. In this case, a specimen used was stood at room temperature (23±3° C.) for 30 minutes or more, and 27±3 g of the specimen was collected and put in a die cavity, and then, Platen was operated and the mooney viscosity was measured while applying torque.

In addition, during measuring the mooney viscosity, the change of the mooney viscosity appearing while releasing torque was observed for 1 minute, and a —S/R value was determined from the gradient value thereof.

TABLE 1

| | | Example 1 | Example 2 | Comparative Example 1 | Comparative Example 2 | Comparative Example 3 |
|---|---|---|---|---|---|---|
| | Modification state | Modified | Modified | Unmodified | Modified | Modified |
| GPC results | Mn (×10$^5$ g/mol) | 3.4 | 3.22 | 3.08 | 3.15 | 3.0 |
| | Mw (×10$^5$ g/mol) | 8.83 | 9.06 | 8.59 | 9.17 | 8.8 |
| | Mw/Mn | 2.60 | 2.8 | 2.4 | 2.91 | 3.3 |

TABLE 1-continued

|  | Example 1 | Example 2 | Comparative Example 1 | Comparative Example 2 | Comparative Example 3 |
|---|---|---|---|---|---|
| MV (ML1 + 4, @100° C.) (MU) | 47 | 48 | 45 | 48 | 54 |
| −S/R | 0.7598 | 0.76 | 0.7 | 0.78 | 0.730 |

As shown in Table 1, the modified butadiene polymers of Example 1 and Example 2 according to exemplary embodiments of the present invention showed —S/R values of 0.7 or more and were found to have high linearity.

Experimental Example 2

A rubber composition and a rubber specimen were manufactured using each of the modified butadiene polymers prepared in the Examples and butadiene polymers prepared in the Comparative Examples, and mooney viscosity, tensile strength, 300% modulus, and viscoelasticity were measured according to the methods below. The results are listed in Table 2 below.

Particularly, each rubber composition was prepared by compounding 100 parts by weight of each of modified butadiene polymers and butadiene polymers with 70 parts by weight of carbon black, 22.5 parts by weight of a process oil, 2 parts by weight of an antiaging agent (TMDQ), 3 parts by weight of zinc white (ZnO), and 2 parts by weight of stearic acid. Then, to each rubber composition, 2 parts by weight of sulfur, 2 parts by weight of a vulcanizing accelerator (CZ) and 0.5 parts by weight of a vulcanization accelerator (DPG) were added and vulcanized at 160° C. for 25 minutes to manufacture a rubber specimen.

1) Mooney Viscosity (ML1+4)

The mooney viscosity was measured for each rubber specimen by using MV2000E of Monsanto Co. using Large Rotor at the conditions of a rotor speed of 2±0.02 rpm at 100° C.

2) Tensile Strength and 300% Modulus

Each rubber composition was vulcanized at 150° C. for t90 minutes, and tensile strength and modulus when elongated by 300% (M-300%) of a vulcanized product were measured based on ASTM D412.

In the present invention, with respect to each measured value, improved degree was index with setting the measured value of Comparative Example 1 to 100. In this case, if tensile strength and 300% modulus values increase, it means that the tensile strength and 300% modulus are improved.

3) Viscoelasticity Properties (Tan δ @0° C. and Tan δ @60° C.)

Tan δ properties that are the major factors of low fuel consumption properties were measured as a viscoelasticity coefficient (Tan δ) at 60° C., at a frequency of 10 Hz, prestrain of 3%, and dynamic strain of 3% by using DMTS 500N of Gabo Co., Germany.

In the present invention, with respect to each measured value, improved degree was indexed with setting the measured value of Comparative Example 1 to 100. In this case, if the viscoelasticity coefficient index value at a low temperature of 0° C. increases, it means that wet skid resistance is excellent, and if the viscoelasticity coefficient index value at a high temperature of 60° C. increases, it means that the hysteresis loss is small and excellent low rolling resistance, i.e., a low fuel consumption ratio is shown.

TABLE 2

| Division | | Example 1 | Example 2 | Comparative Example 1 | Comparative Example 2 | Comparative Example 3 |
|---|---|---|---|---|---|---|
| ML1 + 4 (FMB: Final Master batch) | | 90.3 | 89.4 | 80 | 89 | 89.2 |
| Tensile properties | M-300% Index | 111 | 108 | 100 | 102.8 | 103.4 |
| | Tensile strength Index | 110 | 103 | 100 | 103 | 99 |
| tanδ @0° C. Index | | 106 | 101 | 100 | 100 | 101 |
| tanδ @60° C. Index | | 109 | 106 | 100 | 104 | 102 |

As shown in Table 2, the rubber specimen manufactured using the modified butadiene polymer of the Example prepared using the modifier according to an embodiment of the present invention, showed excellent tensile properties and viscoelasticity properties when compared with the rubber specimen manufactured using the butadiene polymer of the Comparative Example.

Particularly, the rubber specimen manufactured using the modified butadiene polymer of the Example prepared using the modifier according to an embodiment of the present invention, showed an excellent M-300% modulus value and tensile strength when compared with the rubber specimen manufactured using the unmodified butadiene polymer of Comparative Example 1 and the butadiene polymers modified with the modifiers according to Comparative Example 2 and Comparative Example 3

Accordingly, it was found that the rubber specimen including the modified butadiene polymer according to an embodiment of the present invention showed improved mechanical properties such as tensile properties and strength.

In addition, it was found that the rubber specimen manufactured using the modified butadiene polymer of the Example prepared using the modifier according to an embodiment of the present invention, showed improved viscoelasticity properties when compared with the rubber specimens manufactured using the unmodified butadiene polymer of Comparative Example 1 and the butadiene polymers modified with the modifiers according to Comparative Example 2 and Comparative Example 3, through the Tan δ index values at 0° C. and 60° C. The results means that the modified butadiene polymer prepared using the modifier according to an embodiment of the present invention has excellent road surface resistance, excellent rolling resistance, and a high fuel consumption ratio.

Here, the modified butadiene polymer of Comparative Example 2 was prepared using a modifier in which an amine group is protected by an alkyl group which is an inactive substituent, and the modified butadiene polymer of Comparative Example 3 was prepared using a modifier having a tertiary amine group and an ester group but no alkylsilane group, and though a subsequent treatment process is performed, a secondary amine group is not formed in these two modifiers. That is, the modifier according to an embodiment of the present invention includes two ester functional groups and has increased contact probability with the active part of an active butadiene polymer, and thus, has increased modification ratio. In addition, since the modified butadiene polymer having a high modification ratio has an amine group which is protected by a trialkylsilyl group, an even more amount of two secondary amine groups, which are produced through hydrolysis in a subsequent process, may increase, thereby achieving excellent affinity with a filler such as carbon black.

The invention claimed is:

1. A modifier represented by the following Formula 1:

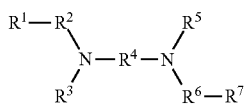
[Formula 1]

in Formula 1,
$R^1$ is —COOR$^8$,
$R^2$ and $R^6$ are each independently a divalent hydrocarbon group of 2 to 20 carbon atoms,
$R^3$ and $R^5$ are each independently —SiR$^9$R$^{10}$R$^{11}$,
$R^4$ is a divalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms, and an aryl group of 6 to 30 carbon atoms,
$R^7$ is —COOR$^{12}$,
where $R^8$ and $R^{12}$ are each independently a monovalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms, and an aryl group of 6 to 30 carbon atoms, and
$R^9$ to $R^{11}$ are each independently a monovalent hydrocarbon group of 1 to 20 carbon atoms, or a monovalent hydrocarbon group of 1 to 20 carbon atoms comprising one or more heteroatoms selected from the group consisting of N, S and O.

2. The modifier according to claim 1, wherein
in Formula 1,
$R^2$ and $R^6$ are each independently an alkylene group of 2 to 10 carbon atoms,
$R^4$ is an alkylene group of 2 to 10 carbon atoms,
$R^8$ and $R^{12}$ are each independently an alkyl group of 1 to 10 carbon atoms, which is unsubstituted or substituted with a linear or branched alkyl group of 1 to 10 carbon atoms, and
$R^9$ to $R^{11}$ are each independently any one selected from the group consisting of an alkyl group of 1 to 10 carbon atoms, a cycloalkyl group of 3 to 12 carbon atoms, an aryl group of 6 to 12 carbon atoms, an arylalkyl group of 7 to 12 carbon atoms, an alkoxyalkyl group of 2 to 10 carbon atoms, a phenoxyalkyl group of 7 to 12 carbon atoms and an aminoalkyl group of 1 to 10 carbon atoms.

3. The modifier according to claim 1, wherein the modifier represented by Formula 1 is a compound represented by the following Formula 2 or Formula 3:

[Formula 2]

[Formula 3]

4. A method for preparing the modifier represented by Formula 1 as in claim 1, the method comprising:
step a: performing first reaction between a compound represented by Formula 4 below and a compound represented by Formula 5 below to prepare a compound represented by Formula 6 below; and
step b: performing second reaction between the compound represented by Formula 6 below and a compound represented by Formula 7 below:

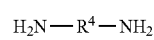
[Formula 4]

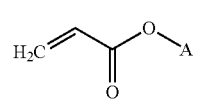
[Formula 5]

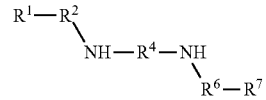
[Formula 6]

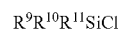
[Formula 7]

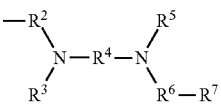
[Formula 1]

in Formulae 1 and 4-7,
$R^1$ is —COOR$^8$,
$R^2$ and $R^6$ are each independently a divalent hydrocarbon group of 2 to 20 carbon atoms,
$R^3$ and $R^5$ are each independently —SiR$^9$R$^{10}$R$^{11}$,
$R^4$ is a divalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms,
$R^7$ is —COOR$^{12}$,
A is $R^8$ or $R^{12}$,
where $R^8$ and $R^{12}$ are each independently a monovalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms, and $R^9$ to $R^{11}$ are each independently a monovalent hydrocarbon group of 1 to 20 carbon atoms, or a monovalent hydrocarbon group of 1 to 20 carbon atoms comprising one or more heteroatoms selected from the group consisting of N, S and O.

5. The method for preparing the modifier according to claim 4, wherein in Formulae 1 and 4 to 7, $R^2$ and $R^6$ are each independently an alkylene group of 2 to 10 carbon atoms, $R^4$ is an alkylene group of 2 to 10 carbon atoms, $R^8$ and $R^{12}$ are each independently an alkyl group of 1 to 10 carbon atoms, which is unsubstituted or substituted with a linear or branched alkyl group of 1 to 10 carbon atoms, and $R^9$ to $R^{11}$ are each independently any one selected from the group consisting of an alkyl group of 1 to 10 carbon atoms, a cycloalkyl group of 3 to 12 carbon atoms, an aryl group of 6 to 12 carbon atoms, an arylalkyl group of 7 to 12 carbon atoms, an alkoxyalkyl group of 2 to 10 carbon atoms, a phenoxyalkyl group of 7 to 12 carbon atoms and an aminoalkyl group of 1 to 10 carbon atoms.

6. The method for preparing the modifier according to claim 4, further comprising a step of adding a base represented by the following Formula 8 in step b:

$$R^{15}R^{16}R^{17}N \qquad \text{[Formula 8]}$$

where $R^{15}$ to $R^{17}$ are each independently a monovalent hydrocarbon group of 1 to 20 carbon atoms.

7. The method for preparing the modifier according to claim 6, wherein the base is one or more selected from triethylamine or diisopropylethylamine.

8. The method for preparing the modifier according to claim 4, wherein the compound represented by Formula 4 and the compound represented by Formula 5 are reacted in a molar ratio of 1:1 to 1:3 (compound represented by Formula 4: compound represented by Formula 5).

9. The method for preparing the modifier according to claim 4, wherein the compound represented by Formula 6 and the compound represented by Formula 7 are reacted in a molar ratio of 1:2 to 1:4 (compound represented by Formula 6: compound represented by Formula 7).

10. The method for preparing the modifier according to claim 4, wherein step a is performed in a temperature range of 5° C. to 60° C.

11. The method for preparing the modifier according to claim 4, wherein step b is performed by adding the compound represented by Formula 7 to the compound represented by Formula 6 in a temperature range of −10° C. to 20° C., and then, increasing the temperature to a temperature range of 0° C. to 35° C.

12. A modified conjugated diene-based polymer comprising a functional group derived from a modifier represented by the following Formula 1:

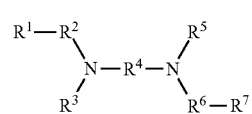

[Formula 1]

in Formula 1, $R^1$ is —COOR$^8$, $R^2$ and $R^6$ are each independently a divalent hydrocarbon group of 2 to 20 carbon atoms, $R^3$ and $R^5$ are each independently —SiR$^9$R$^{10}$R$^{11}$, $R^4$ is a divalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms, $R^7$ is —COOR$^{12}$, where $R^8$ and $R^{12}$ are each independently a monovalent hydrocarbon group of 1 to 20 carbon atoms, which is unsubstituted or substituted with one or more substituents selected from the group consisting of a linear or branched alkyl group of 1 to 20 carbon atoms, a cycloalkyl group of 3 to 20 carbon atoms and an aryl group of 6 to 30 carbon atoms, and $R^9$ to $R^{11}$ are each independently a monovalent hydrocarbon group of 1 to 20 carbon atoms, or a monovalent hydrocarbon group of 1 to 20 carbon atoms comprising one or more heteroatoms selected from the group consisting of N, S and O.

13. The modified conjugated diene-based polymer according to claim 12, wherein the modifier represented by Formula 1 is a compound represented by the following Formula 2 or Formula 3:

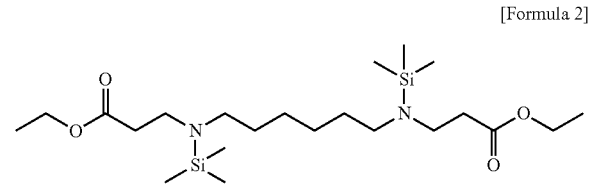

[Formula 2]

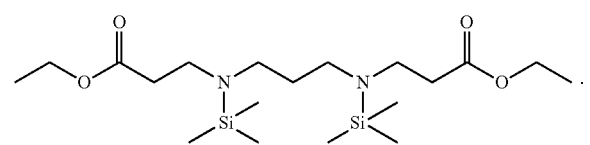

[Formula 3]

14. The modified conjugated diene-based polymer according to claim 12, wherein the polymer has a number average molecular weight (Mn) of 100,000 g/mol to 700,000 g/mol.

15. The modified conjugated diene-based polymer according to claim 12, wherein the polymer has molecular weight distribution (Mw/Mn) of 1.05 to 5.

16. The modified conjugated diene-based polymer according to claim 12, wherein the polymer has a —stress/relation (—S/R) value of 0.7 or more at 100° C.

* * * * *